United States Patent
Frost et al.

(10) Patent No.: US 10,858,318 B2
(45) Date of Patent: Dec. 8, 2020

(54) BORN-BASED CYCLOADDITION CATALYSTS AND METHODS FOR THE PRODUCTION OF BIO-BASED TEREPHTHALIC ACID, ISOPHTHALIC ACID AND POLY (ETHYLENE TEREPHTHALATE)

(71) Applicant: Board of Trustees of Michigan State University, East Lansing, MI (US)

(72) Inventors: John Wesley Frost, Okemos, MI (US); Peng Zhang, Piscataway, NJ (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 15/762,822

(22) PCT Filed: Sep. 23, 2016

(86) PCT No.: PCT/US2016/053236
§ 371 (c)(1),
(2) Date: Mar. 23, 2018

(87) PCT Pub. No.: WO2017/053652
PCT Pub. Date: Mar. 30, 2017

(65) Prior Publication Data
US 2018/0265468 A1    Sep. 20, 2018

Related U.S. Application Data
(60) Provisional application No. 62/232,146, filed on Sep. 24, 2015.

(51) Int. Cl.
| | |
|---|---|
| *C07C 51/347* | (2006.01) |
| *C07D 209/18* | (2006.01) |
| *B01J 31/14* | (2006.01) |
| *C07C 51/353* | (2006.01) |
| *C07C 61/22* | (2006.01) |
| *C07C 61/28* | (2006.01) |
| *C07C 61/39* | (2006.01) |

(52) U.S. Cl.
CPC ............ *C07D 209/18* (2013.01); *B01J 31/14* (2013.01); *B01J 31/146* (2013.01); *C07C 51/347* (2013.01); *C07C 51/353* (2013.01); *C07C 61/22* (2013.01); *C07C 61/28* (2013.01); *C07C 61/39* (2013.01); *B01J 2231/326* (2013.01); *C07C 2601/16* (2017.05); *C07C 2602/42* (2017.05); *C07C 2602/44* (2017.05); *Y02P 20/52* (2015.11)

(58) Field of Classification Search
CPC ................................................. C07C 51/347
See application file for complete search history.

(56) References Cited

U.S. PATENT DOCUMENTS 7,714,149 B2    5/2010 Zhang

FOREIGN PATENT DOCUMENTS

| WO | WO 2014-144843 | 9/2014 | |
|---|---|---|---|
| WO | WO-2014144843 A1 * | 9/2014 | ........... C07C 51/265 |

OTHER PUBLICATIONS

Torre et al. Tetrahedron 1999, 55, 8547-8554 (Year: 1999).*
Furuta et al. J. Am. Chem. Soc. 1988, 110, 6254-6255 (Year: 1988).*
Miller et al. ACS Sustainable Chem. Eng. 2014, 2, 2053-2056 (Year: 2014).*
Larsen et al. J. Chem. Soc. Perkin Trans. 11995, 1019-1028 (Year: 1995).*
Torre, Maria Fe De La et al. 'Application of arylboron di fluoride Lewis acid catalysts to the Diels-Alder reaction: Convenient, non-volatile alternatives to boron trifluoride', Tetrahedron, 1999, vol. 55, pp. 8547-8554.
Zheng, Hongchao et al., 'Mild and efficient boronic acid catalysis of Diels-Alder cycloadditions to 2-alkynoic acids', Tetrahedron Letters, 2010, vol. 51, pp. 3561-3564.
Zhu, Yinghuai et al., 'Application of cycloaddition reactions to the syntheses of novel boron compounds', Molecules, 2010, vol. 15, pp. 9437-9449.
International Search Report for PCT/US2016/053236 dated Jan. 10, 2017.
Wang, Fei et al. "Dehydro-aromatization of cyclohexene-carboxylic acids by sulfuric acid: critical route for bio-based terephthalic acid synthesis," RSC Advances, vol. 4, No. 12, Jan. 1, 2014 (Jan. 1, 2014), p. 6314.
Extended European Search Report for European Patent Application No. 16849651.1, dated Jul. 24, 2019.

* cited by examiner

*Primary Examiner* — Matthew P Coughlin
(74) *Attorney, Agent, or Firm* — King & Spalding

(57) ABSTRACT

Methods for producing cycloaddition products comprising: reacting a diene with a dienophile in the presence of one or more boron-based catalysts of Formula I or Formula II are provided. In particular, the methods can be used to prepare 4-methyl-3-cyclohexene-1-carboxylic acid and 3-methyl-3-cyclohexene-1-carboxylic acid, including bio-based versions thereof. The cycloaddition products can be advantageously used in the production of terephthalic acid and isophthalic acid, and ultimately, poly(ethylene terephthalate), and bio-based versions thereof.

Formula I

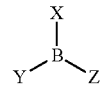

Formula II

BOBL₄

20 Claims, 7 Drawing Sheets

BORN-BASED CYCLOADDITION CATALYSTS AND METHODS FOR THE PRODUCTION OF BIO-BASED TEREPHTHALIC ACID, ISOPHTHALIC ACID AND POLY (ETHYLENE TEREPHTHALATE)

CROSS REFERENCE TO RELATED APPLICATIONS

This application is a national phase application under 35 U.S.C. § 371 of International Application No. PCT/US2016/053236, filed on Sep. 23, 2016, which claims priority to U.S. Provisional Patent Application No. 62/232,146, filed Sep. 24, 2015, the contents of which are incorporated herein by reference.

ACKNOWLEDGEMENT OF GOVERNMENT SUPPORT

This invention was made with government support under CHE1213299 awarded by the National Science Foundation. The government has certain rights in the invention.

FIELD OF THE ART

The present invention relates to catalysts useful in cycloaddition reactions for dienes and unesterified acrylic acid compounds, and methods for the synthesis of bio-based terephthalic acid, isophthalic acid, poly(ethylene terephthalate) (PET), and bio-based versions thereof.

BACKGROUND

Plastic bottles are used to package a variety of consumer products, including food, beverage, cosmetic, personal care, and cleaning products. On average, every person uses about 168 plastic water bottles every year, with over 100 million water bottles used worldwide every day. The U.S. population alone uses about 60 million plastic water bottles every day. In Europe, another 30 million plastic water bottles are used daily.

Increased concern regarding environmental problems and climate change has led to a heightened awareness of the composition of products, how they are made, and how they are disposed of. PET, the plastic used to make most beverage bottles, is conventionally derived from petroleum, which is a non-renewable resource. Moreover, it takes about 700 years for a conventional PET bottle to begin to decompose, and up to 1000 years to fully decompose. Given the environmental problems associated with conventional PET packaging, there is interest in producing PET and other plastic packaging from biomass.

PET is produced by polymerization of terephthalic acid with ethylene glycol. Isophthalic acid is added to the polymerization at about 5% (by weight) to inhibit crystallization. The terephthalic acid and isophthalic acid used to synthesize PET are typically derived from xylene, which is conventionally isolated from BTX aromatics (benzene, toluene, and ortho-, meta-, and para-xylene) produced from crude oil. Over 150 billion liters of oil are used each year for plastic bottle manufacturing.

Terephthalic acid and isophthalic acid can be synthesized from isoprene and acrylic acid. A synthesis of terephthalic acid and isophthalic acid involves a pathway that begins with a cycloaddition reaction between isoprene and acrylic acid that yields 3-methyl-3-cyclohexene-1-carboxylic acid and 4-methyl-3-cyclohexene-1-carboxylic acid, which can be converted to terephthalic acid and isophthalic acid. The starting materials, i.e., isoprene and acrylic acid, can be produced from renewable resources. Bio-isoprene can be produced by fermenting microbes growing in a biomass feedstock. Bio-acrylic acid can be produced by fermenting genetically modified microbes on a biomass feedstock of dextrose (corn) or sucrose (cane).

In order to enhance selectivity for the para cycloadduct of the reaction between isoprene and acrylic acid, various Lewis acid catalysts have been used. However, undesired isoprene polymerization, catalyzed by acrylic acid, is accelerated. Esterifying acrylic acid avoids diene polymerization but is not economical.

Only a limited number of catalysts have been successfully employed in Diels-Alder reactions of unesterified acrylic acids (see, for example, K. K. Miller et al. *ACS Sustainable Chem. Eng.* 2014, 2, 205; International Publication No. WO 2014/144843 to J. W. Frost; K. Furata et al. *J. Am. Chem. Soc.* 1988, 110, 6254; R. M. Al-Zoubi et al. *Angew. Chem. Int. Ed.* 2008, 47, 2876; D. Hall et al. U.S. Pat. No. 8,822,720; H. Zheng et al. *Aldrichchimica Acta* 2014, 47, 41; W. H. Miles et al. *Synth. Commun.* 2013, 43, 1980; D. H. Ryu et al. *J. Am. Chem. Soc.* 2002, 124, 9992).

There remains a need for catalysts and processes that utilize isoprene and acrylic acid to generate terephthalate and isophthalate, and in particular, bio-based versions thereof, in an efficient and cost-effective manner. In particular, there remains a need for catalysts and processes that could be used to produce the 36×109 kg/y of terephthalic acid currently synthesized from p-xylene and used in the manufacture of poly(ethylene terephthalate) (PET) to instead be synthesized via cycloaddition of bio-based acrylic acid and bio-based isoprene. Such catalysts and processes would enable the production of PET packaging partially or fully derived from renewable feedstocks.

BRIEF SUMMARY

According to the embodiments, the exemplary catalysts can be used to facilitate high-yielding Diels-Alder reaction of dienophiles, for example unesterified acrylic acids, with dienes under substantially solvent free or highly concentrated reaction conditions. Polymerization reactions, which compete with most Lewis-acid catalyzed cycloadditions of unesterified acrylic acids are substantially avoided or minimized. In certain embodiments, the exemplary catalysts can be used advantageously to selectively catalyze the Diels-Alder reaction of acrylic acid and isoprene. Such reactions can be carried out at mild or ambient temperatures to produce high yields of substantially the para cycloadduct.

In view of the foregoing, one or more embodiments described herein include: methods for producing a cycloaddition product comprising: reacting a diene with a dienophile in the presence of one or more catalysts of Formula I or Formula II;

wherein a catalyst of Formula I has the following structure:

Formula I wherein each X, Y and Z is independently H, F, Cl, Br, I, OC(=O)R$^1$, OR$^1$, substituted or unsubstituted C$_{1-6}$ alkyl, substituted or unsubstituted C$_{6-12}$ aryl; wherein R$^1$ is a substituted or unsubstituted C$_{1-6}$ alkyl; or a substituted or unsubstituted C$_{6-12}$ aryl; and wherein the catalyst is not BH$_3$, BBr$_3$, BCl$_3$, or B(o-bromophenyl)(OH)$_2$; and wherein a catalyst of Formula II has the following structure:

BOBL$_4$                       Formula II wherein each L is independently selected from the group consisting of OC(=O)R$^2$, substituted or unsubstituted C$_{6-12}$ aryl, substituted or unsubstituted C$_{1-6}$ alkyl, substituted or unsubstituted C$_{5-12}$ cycloalkyl; substituted or unsubstituted C$_{1-6}$ alkylsulfonate; substituted or unsubstituted C$_{6-12}$ arylsulfonate, and substituted or unsubstituted C$_{5-12}$ heteroaryl; and wherein R$^2$ is a substituted or unsubstituted C$_{1-6}$ alkyl; or a substituted or unsubstituted C$_{6-12}$ aryl.

In certain embodiments, the cycloaddition reactions are useful in the preparation of 4-methyl-3-cyclohexene-1-carboxylic acid and 3-methyl-3-cyclohexene-1-carboxylic acid, including bio-based versions thereof. The cycloaddition products can be advantageously used in the production of terephthalic acid and isophthalic acid, and ultimately, PET, and bio-based versions thereof. Methods for producing terephthalic acid, isophthalic acid, PET, and bio-based versions thereof, as well as methods for producing bio-based PET articles, containers and preforms, are also provided.

The disclosure may be understood more readily by reference to the following detailed description of the various features of the disclosure and the examples included therein.

DETAILED DESCRIPTION

Figure 1:
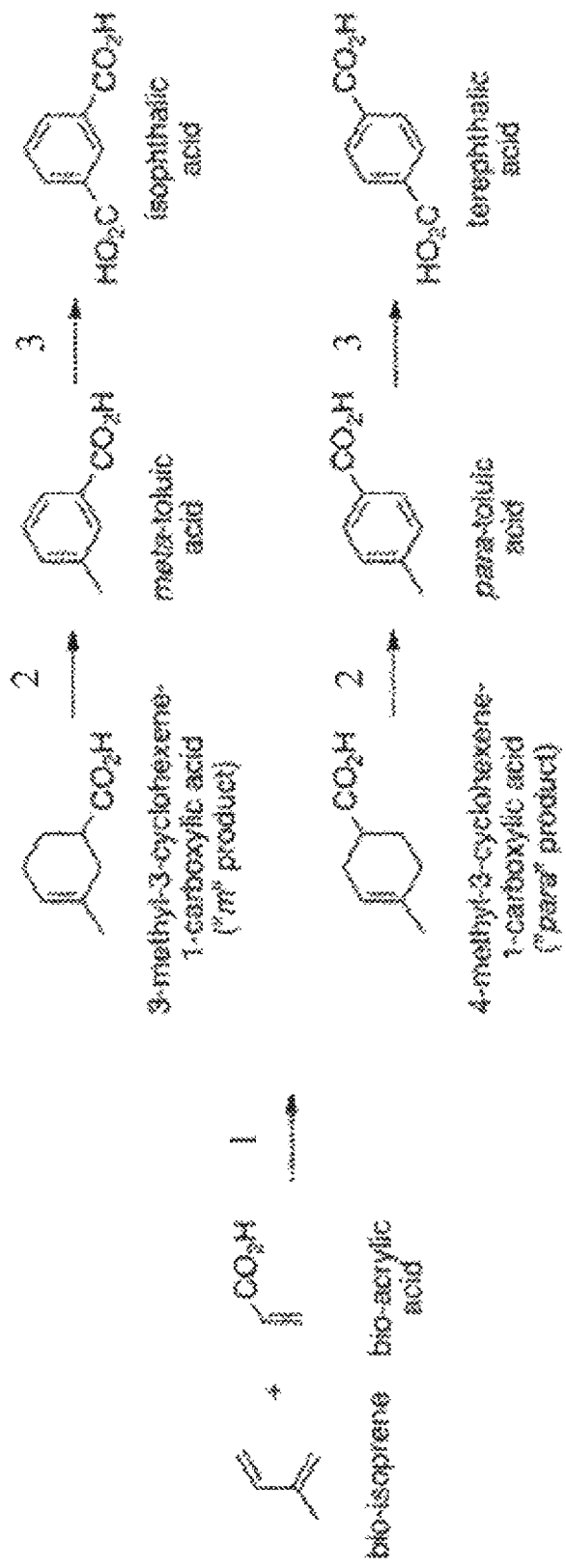
FIG. 1 is a reaction scheme for the production of bio-terephthalic acid and bio-isophthalic acid, wherein a cycloaddition reaction according to the embodiments could be used to facilitate step 1.

Generally, the exemplary methods comprise a Diels-Alder cycloaddition reaction in which a diene reacts with a dienophile in the presence of one or more catalysts of Formula I or Formula II, as described herein, to form a substituted cyclohexene product. The methods comprising the cycloaddition reaction, in conjunction with additional steps, can be used advantageously to produce terephthalic acid, isophthalic acid and mixtures thereof. In such embodiments where the cycloaddition reaction includes a bio-diene and a bio-dienophile, the methods can be used to produce, for example, bio-terephthalic acid, bioisophthalic acid and mixtures thereof, which can be used, for example, in the preparation of bio-based PET.

As used herein, the term "PET" refers to polyethylene terephthalate, its copolyesters, and combinations thereof in any form.

The term "bio-based," as used herein, indicates the inclusion of some component that partially or totally derives from at least one bio-based material. As an example, a "bio-based PET" would be a PET that comprises at least one component (e.g., terephthalic acid, ethylene glycol, isophthalic acid) that partially or totally derives from at least one bio-based material. The term "bio-based materials" and "renewable materials" both refer to organic materials in which the carbon comes from non-fossil biological sources. Bio-based materials may be made from plant materials or through fermentation or other microbial production processes.

In exemplary embodiments, a method for producing a cycloaddition product is provided, the method comprising: reacting a diene with a dienophile in the presence of one or more catalysts of Formula I or Formula II. In exemplary embodiments, the method further comprises producing a mixture of cycloaddition products. In exemplary embodiments, the one or both of the diene and dienophile are bio-based. In exemplary embodiments, the cycloaddition product is a carboxy-substituted cyclohexene compound. In exemplary embodiments, the dienophile comprises a —CH=CHC(O)OH group.

In exemplary embodiments, a method for forming a carboxy-substituted cyclohexene compound is provided, the method comprising: reacting a diene and a dienophile comprising a —CH=CHC(O)OH group in the presence of one or more catalysts of Formula I or Formula II described herein to form a carboxy-substituted cyclohexene compound. In certain embodiments, the method produces a mixture of carboxy-substituted cyclohexene compounds.

In exemplary embodiments, a method for producing 4-methyl-3-cyclohexene-1-carboxylic acid is provided, the method comprising: reacting isoprene with acrylic acid in the presence of one or more catalysts of Formula I or Formula II. In exemplary embodiments, the method further comprises producing 3-methyl-3-cyclohexene-1-carboxylic acid. In exemplary embodiments, the isoprene and the acrylic acid are bio-based.

In exemplary embodiments, a method for producing 4-methyl-3-cyclohexene-1-carboxylic acid, 3-methyl-3-cyclohexene-1-carboxylic acid, or a mixtures thereof, is provided; the method comprising: reacting isoprene with acrylic acid in the presence of one or more catalysts of Formula I or Formula II described herein to form 4-methyl-3-cyclohexene-1-carboxylic acid, 3-methyl-3-cyclohexene-1-carboxylic acid, or a mixtures thereof.

As will be known to those of skill in the art, a Diels-Alder reaction is an organic chemical reaction (specifically, a [4+2] cycloaddition) between a conjugated diene and a substituted alkene, commonly termed the dienophile, to form a substituted cyclohexene system.

Diene

As referred to herein, a "diene" is a C$_4$-C$_{17}$ hydrocarbon that contains at least two carbon double bonds which are separated by a single bond; i.e. two double bonds are conjugated. The diene can be either open-chain or cyclic, and it can host many different types of substituents. The diene compound is not limited to compounds which include two double bonds in their formal structure, and may include other double bonds or compounds that are fully or partially aromatic. Generally, the two double bonds of the diene that participate in the cycloaddition must exist in the cis conformation, since this is the only conformer that can participate in the reaction. In exemplary embodiments, the diene is any diene compound, not particularly limited by carbon chain length or branching, that is liquid at or near ambient temperature or about 20° C. to about 25° C. In exemplary embodiments, the diene is isoprene (2-methyl-1,3-butadiene); 2,3-dimethyl-1,3-butadiene; 1,3-butadiene; piperylene (1,3-pentadiene); 1,3-cyclohexadiene; 1,3-cyclopentadiene; indole (2,3-benzopyrrole) and including any bio-derived sources thereof. In certain embodiments, the diene is isoprene or bio-isoprene. In exemplary embodiments, the diene is a bio-diene.

Dienophile

As referred to herein, a "dienophile" is a $C_3$-$C_{12}$ alkene. Preferably, the dienophile comprises an electron-withdrawing group, such as a carboxy group, in conjugation with the alkene. The dienophile may optionally include additional substituents, for example alkyl, acyl, substituted alkyl, or substituted acyl. In certain embodiments, the dienophile does not include an ester moiety. In exemplary embodiments, the dienophile is an alkene, a bio-alkene, a substituted alkene, a substituted bio-alkene, acrylic acid, bio-acrylic acid, a substituted acrylic acid, a substituted bio-acrylic acid. In certain embodiments, the acrylic acid, bio-acrylic acid, substituted acrylic acid, or substituted bio-acrylic acid is not esterified, i.e. is an unesterified acrylic acid or unesterified substituted acrylic acid. In exemplary embodiments, the dienophile is acrylic acid, or bio-acrylic acid. In exemplary embodiments, the dienophile is a bio-based dienophile.

In exemplary embodiments, the dienophile comprises a —CH=CHC(O)OH group. In exemplary embodiments, the dienophile comprising a —CH=CHC(O)OH group is acrylic acid; a β-acylacrylic acid, such as crotonic acid (trans-2-butenoic acid), 2-bromoacrylic acid, 2-chloroacrylic acid, 3-bromoacrylic acid, 3-chloroacrylic acid, malonate semialdehyde, and including any bio-derived sources thereof.

Catalysts

In exemplary embodiments, a catalyst for use in a Diels-Alder cycloaddition reaction in which a diene reacts with a dienophile is provided, wherein the catalyst influences the ratio of para:meta products formed form the cycloaddition reaction. In exemplary embodiments, the catalyst facilitates the formation of at least about 88%, about 89%, about 90%, about 91%, about 92%, about 93%, about 94%, about 95%, or about 95% yield of the para product. In exemplary embodiments, the catalyst facilitates the formation of at least about 88% to about 100%, about 90% to about 98%, or about 94% to about 97% yield of the para product.

In exemplary embodiments, the catalyst is a compound of Formula I:

Formula I wherein each X, Y and Z is independently H, F, Cl, Br, I, OC(=O)$R^1$, O$R^1$, substituted or unsubstituted $C_{1-6}$ alkyl, substituted or unsubstituted $C_{6-12}$ aryl;

wherein $R^1$ is a substituted or unsubstituted $C_{1-6}$ alkyl; or a substituted or unsubstituted $C_{6-12}$ aryl; and wherein the catalyst is not $BH_3$, $BBr_3$, $BCl_3$, or B(o-bromophenyl)(OH)$_2$.

In exemplary embodiments, at least one of X, Y and Z is Cl. In exemplary embodiments, at least two of X, Y and Z are Cl. In exemplary embodiments, at least one of X, Y and Z is OC(=O)$R^1$, for example OC(=O)$CH_3$ or OC(=O)$CF_3$. In certain embodiments, X is Cl, Y is Cl and Z is OC(=O)$R^1$. In certain embodiments, X is Br, Y is Br and Z is OC(=O)$R^1$. In exemplary embodiments, at least one of X, Y and Z is substituted or unsubstituted $C_{6-12}$ aryl, for example phenyl (—$C_6H_5$). In certain embodiments, the catalyst does not comprise $BF_3$.

In exemplary embodiments, $R^1$ is unsubstituted $C_{1-6}$ alkyl, for example a methyl, ethyl, propyl, butyl, pentyl or hexyl group. In exemplary embodiments, $R^1$ is $CH_3$. In exemplary embodiments, $R^1$ is a substituted $C_{1-6}$ alkyl, for example a $C_{1-6}$ haloalkyl. In exemplary embodiments, $R^1$ is $CF_3$.

In exemplary embodiments, $R^1$ is unsubstituted $C_{6-12}$ aryl, for example phenyl. In exemplary embodiments, $R^1$ is substituted $C_{6-12}$ aryl, for example bromophenyl, chlorophenyl, fluorophenyl, or iodophenyl.

In exemplary embodiments, the compound is $Cl_2B(OC(=O)CH_3)$ (also referred to herein as "$Cl_2BOAc$"). In exemplary embodiments, the compound is $Cl_2B(OC(=O)CF_3)$ (also referred to herein as "$Cl_2BOTFAc$").

In exemplary embodiments, the compound is $(C_6H_5)_2B(OH)$ ((also referred to herein as "$Ph_2BOH$") or a dehydrated form thereof.

In exemplary embodiments, the catalyst is a compound of Formula II:

$$BOBL_4 \qquad \text{Formula II}$$

wherein each L is independently selected from the group consisting of OC(=O)$R^2$, substituted or unsubstituted $C_{6-12}$ aryl, substituted or unsubstituted $C_{1-6}$ alkyl, substituted or unsubstituted $C_{5-12}$ cycloalkyl; substituted or unsubstituted $C_{1-6}$ alkylsulfonate; substituted or unsubstituted $C_{6-12}$ arylsulfonate, and substituted or unsubstituted $C_{5-12}$ heteroaryl; and wherein $R^2$ is a substituted or unsubstituted $C_{1-6}$ alkyl; or a substituted or unsubstituted $C_{6-12}$ aryl.

Catalysts of Formula II can exist as different constitutional isomers depending on the identity of L. Generally, for compounds of Formula II, the oxygen is bonded to both borons and each L is independently bonded to one or both borons. In certain embodiments, each L interacts with only one boron, as depicted by the structure in Formula IIa.

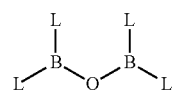

Formula IIa

One example of a catalyst of Formula IIa is BOB($C_6H_5$)$_4$.

Figure 7:
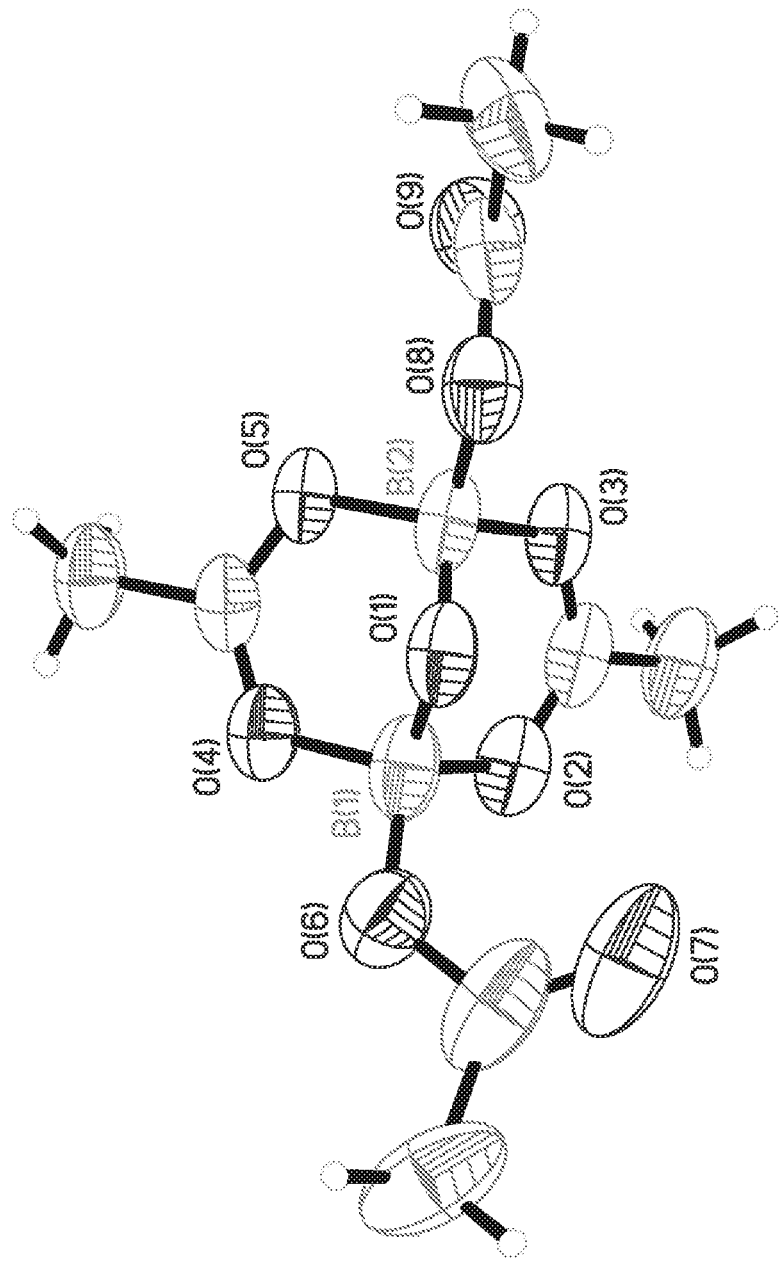
FIG. 7 shows the crystal structure of an exemplary catalyst, BOB(OAc)$_4$.

In other embodiments, when L is a ligand that is capable of forming a bridge across the B—O—B group by interacting with both borons, two L groups may interact only with one boron while the other two L groups may forms bridges such that they each interact with both borons, as depicted by Formula IIb and as shown in FIG. 7.

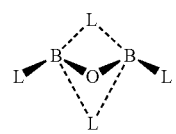

Formula IIb

One example of a catalyst of Formula IIb is a compound of the structure BOB(OC(=O)$R^2$)$_4$, such as BOB(OC(=O)$CH_3$)$_4$.

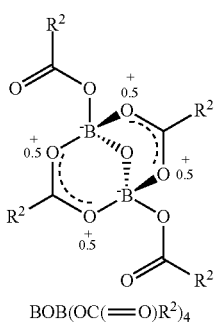

BOB(OC(=O)R$^2$)$_4$

In exemplary embodiments, the catalyst is a compound of Formula IIa:

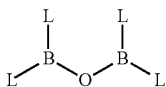

Formula IIa wherein each L is independently selected from the group consisting of OC(=O)R$^2$, substituted or unsubstituted C$_{6-12}$ aryl, substituted or unsubstituted C$_{1-6}$ alkyl, substituted or unsubstituted C$_{5-12}$ cycloalkyl; substituted or unsubstituted C$_{1-6}$ alkylsulfonate; substituted or unsubstituted C$_{6-12}$ arylsulfonate, and substituted or unsubstituted C$_{5-12}$ heteroaryl; and wherein R$^2$ is a substituted or unsubstituted C$_{1-6}$ alkyl; or a substituted or unsubstituted C$_{6-12}$ aryl.

In exemplary embodiments, the catalyst is a compound of Formula IIb:

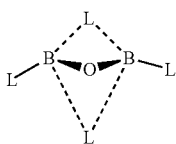

Formula IIb wherein each L is independently selected from the group consisting of OC(=O)R$^2$, substituted or unsubstituted C$_{6-12}$ aryl, substituted or unsubstituted C$_{1-6}$ alkyl, substituted or unsubstituted C$_{5-12}$ cycloalkyl; substituted or unsubstituted C$_{1-6}$ alkylsulfonate; substituted or unsubstituted C$_{6-12}$ arylsulfonate, and substituted or unsubstituted C$_{5-12}$ heteroaryl; and wherein R$^2$ is a substituted or unsubstituted C$_{1-6}$ alkyl; or a substituted or unsubstituted C$_{6-12}$ aryl.

In exemplary embodiments of the foregoing embodiments, R$^2$ is unsubstituted C$_{1-6}$ alkyl, for example a methyl, ethyl, propyl, butyl, pentyl or hexyl group. In exemplary embodiments, R$^2$ is CH$_3$. In exemplary embodiments, R$^2$ is a substituted C$_{1-6}$ alkyl, for example a C$_{1-6}$ haloalkyl. In exemplary embodiments, R$^2$ is CF$_3$.

In exemplary embodiments, R$^2$ is unsubstituted C$_{6-12}$ aryl, for example phenyl. In exemplary embodiments, R$^2$ is substituted C$_{6-12}$ aryl, for example bromophenyl, chlorophenyl, fluorophenyl, or iodophenyl.

In exemplary embodiments, all Ls are the same group. In exemplary embodiments, each L is OC(=O)R$^2$, for example OC(=O)CH$_3$, OC(=O)CF$_3$, or OC(=O)(phenyl). In exemplary embodiments, each L is substituted or unsubstituted C$_{6-12}$ aryl, for example phenyl or halophenyl. In exemplary embodiments, each L is substituted or unsubstituted C$_{1-6}$ alkylsulfonate, for example OS(=O)$_2$CH$_3$ or OS(=O)$_2$CF$_3$. In exemplary embodiments, each L is substituted or unsubstituted C$_{6-12}$ arylsulfonate, for example OS(=O)$_2$(tolyl).

In exemplary embodiments, each L is OC(=O)CH$_3$. In exemplary embodiments, the compound is BOB(OC(=O)CH$_3$)$_4$ (also referred to herein as "BOBOAc$_4$").

In exemplary embodiments, each L is C$_6$H$_5$. In exemplary embodiments, the compound is BOB(C$_6$H$_5$)$_4$ (also referred to herein as "BOBPh$_4$").

In certain embodiments, the one or more catalysts of Formula I or Formula II are selected from the group consisting of: BOB(OAc)$_4$, BOBPh$_4$, Cl$_2$BOTFAc, and Cl$_2$BOAc. In certain embodiments, the one or more catalysts used in the cycloaddition reaction does not comprise 2-bromophenyl boronic acid.

Catalysts can be used to influence the ratio of para:meta products formed form the cycloaddition reaction. In exemplary embodiments, the ratio of para to meta products produced from the cycloaddition reaction is controlled by use of an exemplary catalyst according to the embodiments.

For comparison, with no catalyst present, combining isoprene and acrylic acid (collectively, the "reaction mixture") at a 1:1 molar ratio and then autoclaving at 95° C. for about 2 hours results in the production of 75:25 para:meta product. By repeatedly recrystallizing the para product from cold hexane (0° C.-5° C.), pure para product can be isolated at about a 59% yield.

Catalysis leading to acyloxyborane and acylboronate intermediacy can enhance para selectivity in the cycloaddition of acrylic acid and isoprene. Use of BH$_3$ (15 mol) and 2-bromophenylboronic acid (20 mol) affords 80-90% yields of 4-methyl-3-cyclohexene-1-carboxylic acid (para product) cycloaddition product in CH$_2$Cl$_2$. However, the solvent choice, relatively high mol % catalyst requirement, and the multiple steps/expense for synthesis of BH$_3$ and 2-bromophenylboronic acid detracts from their potential utility in commodity chemical synthesis. Catalysis of the cycloaddition reaction with the exemplary catalysts is an attractive alternative.

In exemplary embodiments, the one or more catalysts of Formula I or Formula II as used in the cycloaddition reactions produces a higher fraction of para cycloaddition products than meta products. In certain embodiments, the yield of para cycloaddition products produced by the cycloaddition reactions according to the embodiments is greater than about 90%, about 91%, about 92%, about 93%, about 94%, about 95%, or about 96%. In certain embodiments, yield of meta cycloaddition products produced by the cycloaddition reactions according to the embodiments is less than about 5%, about 4%, about 3%, about 2%, or about 1%. In certain embodiments, the cycloaddition reactions according to the embodiments produce less than about 6%, about 5%, about 4%, about 3%, about 2%, or about 1% side reaction products, for example polymerization products or 3-chloropropionic acid. In certain embodiments, the cycloaddition reaction yields about 90 to 100% para and about 0 to about 10% meta products.

In exemplary embodiments, the one or more catalysts of Formula I or Formula II as used in the cycloaddition reactions produces a higher fraction of endo cycloaddition products than exo products. In certain embodiments, the yield of endo cycloaddition products produced by the cycloaddition reactions according to the embodiments is greater than about 60%, about 70%, about 80%, about 90%, about 94%, about 95%, or about 96%. In certain embodiments, the yield of exo cycloaddition products produced by the cycloaddition reactions according to the embodiments is less than about 27%, about 20%, about 15%, about 10%, about 5%, or about 1%.

In exemplary embodiments, the cycloaddition is conducted under neat conditions, i.e., as a reaction conducted essentially without solvents or substantially in the absence of solvents. Such reaction conditions are advantageous, avoiding potential toxicity, volatility, and recycling issues that may be associated with solvent use. Therefore, in various embodiments, the cycloaddition reaction can be performed under neat reaction conditions in the presence of an exemplary catalyst according the embodiments. In certain embodiments, the cycloaddition of a diene, e.g. isoprene, and a dienophile, e.g. acrylic acid, is a neat reaction using one or more catalysts of Formula I or Formula II. In exemplary embodiments, the cycloaddition reaction is carried out substantially in the absence of solvent or under substantially solvent-free conditions.

In exemplary embodiments, the cycloaddition reaction is carried out in a minimum amount of one or more solvents, for example heptane or tetrahydrofuran. In certain embodiments, the cycloaddition of a diene, e.g. isoprene, and a dienophile, e.g. acrylic acid, is carried out using one or more catalysts of Formula I or Formula II and a minimum amount of solvent, for example the solvent necessary to transfer and/or dissolve the catalyst.

In exemplary embodiments, the catalyst is used in the form of a dry solid or a solution, for example a highly concentrated solution or a solution in the range about 0.1M to about 5M, or about 0.15M to about 1M.

In exemplary embodiments, the reaction is carried out by combining the dienophile and the one or more catalysts of Formula I or Formula II, followed by addition of diene. In other exemplary embodiments, the reaction is carried out by combining the dienophile and the diene, followed by addition of the one or more catalysts of Formula I or Formula II.

In certain embodiments, the one or more catalysts of Formula I or Formula II, are at least partially synthesized in the presence of the diene and dienophile. For example, in certain embodiments, the diene, dienophile and a silver salt, such as silver acetate or silver trifluoroacetate, followed by the addition of a boron trihalide reagent, such as $BCl_3$.

In exemplary embodiments, the cycloaddition reaction may be conducted at a temperature from about −30° C. to about 30° C., about 0° C. to about 30° C., or about 20° C. to about 25° C. In exemplary embodiments, the reaction proceeds for from at least about 1 hour, at least about 10 hours, or at least about 24 hours. In various embodiments, the reaction proceeds for about 120 hours or less, for about 100 hours or less, or for from about 48 hours or less. In some embodiments, the reaction is conducted at ambient (room temperature) conditions (i.e., at from about 20° C. to about 25° C.), for from about 1 hour to about 48 hours. In some embodiments, the reaction is initiated at a reduced temperature, such as from about −20° C. to about 0° C., and then allowed to warm to room temperature where the reaction proceeds for from about 1 hour to about 48 hours.

In exemplary embodiments, the method produces substantially 4-methyl-3-cyclohexene-1-carboxylic acid.

In exemplary embodiments, the cycloaddition reaction is carried out with about 2 to about 10 mole % of a catalyst described herein. In exemplary embodiments, that catalyst is added to the reaction vessel in the form of a solution, for example a solution in heptane or tetrahydrofuran. In certain embodiments, the catalyst is added to the reaction vessel without the addition of solvent.

In exemplary embodiments, the diene is used neat or at a concentration of about 0.5 to about 5M. In exemplary embodiments, the dienophile is used neat or at a concentration of about 0.5 to about 5M in a solvent, for example heptane, THF, methylene chloride or toluene.

In exemplary embodiments, the cycloaddition reaction is not substantially air- or moisture-sensitive. In certain embodiments, the cycloaddition reaction is carried out in the presence of air or atmospheric moisture. In exemplary embodiments, the cycloaddition reaction may be carried out under an inert gas, such as Ar, Ne, or He.

In exemplary embodiments, the catalyst can be used to enhance formation of the para cycloadduct. Without being bound by theory, the catalyst may form a complex with an acrylate carbonyl oxygen to facilitate selection formation of the para cycloadduct in Diels-Alder reactions with dienes such as isoprene while minimizing competing polymerization reactions. In exemplary embodiments, the catalysts of Formula I or II can be used in the cycloaddition reactions to minimize competing polymerization reactions.

In exemplary embodiments, one or more additional catalysts can be used in the cycloaddition reaction. In certain embodiments, the one or more catalysts do not comprise $TiCl_4$ and $BH_3$.

Synthesis of Terephthalic Acid and Isophthalic Acid

As shown in FIG. 1, a reaction scheme for the production of terephthalic acid and isophthalic acid comprises a cycloaddition, an aromatization, and an oxidation. The meta product of the cycloaddition reaction 3-methyl-3-cyclohexene-1-carboxylic acid and the para product is 4-methyl-3-cyclohexene-1-carboxylic acid. When bio-isoprene and bio-acrylic acid are the starting reactants, terephthalic acid and isophthalic acid are downstream products of the para and meta products of the cycloaddition, respectively. Methods for carried out the aromatization and oxidation steps of the reaction are known in the art, for example in the disclosure of International Publication No. WO 2014/144843, which is incorporated by reference in its entirety.

In exemplary embodiments, the isoprene and acrylic acid are bio-based, i.e., are bio-isoprene and bio-acrylic acid, to make bio-based terephthalic acid and isophthalic acid. Bio-based materials may be made from plant materials or through fermentation or other microbial production processes.

Bio-Isoprene

In one embodiment, the isoprene used in the method of the present invention is petroleum-based. In another embodiment, the isoprene used in the method of the present invention is bio-based.

Isoprene is conventionally recovered from pyrolysis gasoline in naphtha cracking to produce ethylene, by a series of fairly capital intensive steps. Initially cyclopentadiene is removed from the pyrolysis gasoline by dimerization and distillation. Subsequently, pipirylenes are separated out by superfractionation, and the isoprene (at 10 to 20% of the pyrolysis gasoline) is then recovered by extractive distillation using a solvent. In recent years, however, with the availability of abundant, inexpensive natural gas, ethylene has increasingly been produced using lighter feedstocks for the steam crackers so that pyrolysis gasoline production has declined. A number of other petroleum processing-based or -dependent routes to isoprene have been developed as well.

Production of bio-isoprene from renewable resources is also known, wherein the bio-isoprene is partially or totally bio-based. For example, it is known to produce isoprene using isobutanol produced using biomass as a primary feedstock, as an isobutene precursor. It is also known to bio-based isoprene using genetically-engineered microorganisms. The biotransformation process a microorganism with sufficient capabilities to support the fermentation of glucose—possibly sucrose and other sugars—from renewable resources into isoprene. Pathways that drive the reaction away from isoprene are attenuated and those that drive the reaction toward isoprene production are enhanced. The bio-derived isoprene generated needs to be recovered and purified to a suitable specification. For example, Whited et al. (Ind. Biotechnol., 2010; 6(3): 152-163) describe various platforms for generating bio-isoprene from in engineered bacteria from renewable feedstocks. These platforms include engineered recombinant bacteria that have a heterologous isoprene synthase gene, which is derived from plants. Hayashi et al. (International Publication No. WO 2013/178722) describe methods for producing bio-isoprene monomer in various bacteria and fungi with various saccharides as a source of carbon. These methods include engineering bacteria and fungi with an isoprene synthase gene from plants, which enables the bacteria and fungi to biosynthesize isoprene. Whited et al. and Hayashi et al. are both incorporated herein by reference in their entirety.

Bio-Acrylic Acid

In one embodiment, the acrylic acid used in the method of the present invention is petroleum-based. In another embodiment, the acrylic acid used in the method of the present invention is bio-based.

Conventionally, acrylic acid is produced from petroleum. It is also known to produce acrylic acid from renewable resources and more particularly, by means of fermentation. Bio-acrylic acid, may be made by fermenting genetically modified microbes on a biomass feedstock of dextrose (corn) or sucrose (cane). For example, Kumar et al. (Biotechnol. Adv., 2013; 31:945-961) describe various methods for synthesizing 3-hydroxypropionic acid (3-HP), which can be converted into acrylic acid, from various prokaryotes and eukaryotes. Also, Devroe et al. (U.S. Patent Application Publication No. 2009/0203070) describe methods for producing bio-acrylic acid from hyperphotosynthetic organisms, such as various plants, algae, and bacteria. Additionally, Lynch et al., (U.S. Patent Application Publication No. 2013/0071893), describe a process for generating bio-acrylic acid from recombinant bacterial and yeast microorganisms, which rely on various monosaccharides (such as glucose and fructose), oligosaccharides (such as lactose and sucrose), and polysaccharides (such as starch and cellulose) as sources of carbon. Kumar et al., Devroe et al, and Lynch et al. are all incorporated herein by reference in their entirety.

In exemplary embodiments, the diene is bio-isoprene and the dienophile is bio-acrylic acid. Referring again to FIG. 1, when the diene is bio-isoprene and the dienophile is bio-acrylic acid, bio-isoprene and bio-acrylic acid undergo a cycloaddition reaction to form 4-methyl-3-cyclohexene-1-carboxylic acid (the para product) and 3-methyl-3-cyclohexene-1-carboxylic acid (the meta product). In some embodiments, the cycloaddition reaction according to the embodiments is performed to yield a para-product:meta-product ratio that ultimately yields a terephthalic acid: isophthalic acid ratio useful for PET production. For example, because the synthesis of PET requires about 95% terephthalic acid and about 5% isophthalic acid, in various embodiments the cycloaddition reaction is performed to result in a para product:meto product ratio of about 10:1. In other embodiments, the para:meta product ratio is about 49:1, about 40:1, about 30:1, about 20:1, about 10:1, about 5:1, about 4:1, about 3:1, or about 2:1. In exemplary embodiments, the para:meta product ratio is in the range of about 2:1 to about 49:1.

In exemplary embodiments, a method for producing terephthalic acid, isophthalic acid or a mixture thereof is provided, the method comprising:
(a) reacting isoprene with acrylic acid in the presence of one or more catalysts of Formula I or Formula II described herein to form 4-methyl-3-cyclohexene-1-carboxylic acid, 3-methyl-3-cyclohexene-1-carboxylic acid, or a mixtures thereof;
(b) performing an aromatization reaction on the 4-methyl-3-cyclohexene-1-carboxylic acid, 3-methyl-3-cyclohexene-1-carboxylic acid, or a mixtures thereof to form a second product selected from the group consisting of para-toluic acid, meta-toluic acid, and mixtures thereof; and
(c) performing an oxidation reaction on the second product to form terephthalic acid, isophthalic acid, or mixtures thereof.

In exemplary embodiments, the methods described herein can be used to prepare bio-terephthalic acid or bio-isophthalic acid.

(2) Aromatization Step

In exemplary embodiments, the aromatization of the product of the cycloaddition reaction, may be carried out by any means necessary or known to those of skill in the art. With reference to FIG. 1, the aromatization reaction can be a solvent phase reaction, an oxidative dehydrogenation, or a vapor phase reaction. For example, the aromatization may comprise an $H_2SO_4$ oxidation of the para and meta cycloaddition products to form para-toluic acid and meta-toluic acid. In an $H_2SO_4$ oxidation, concentrated sulfuric acid may be added dropwise to one or both of 4-methyl-3-cyclohexene-1-carboxylic acid and 3-methyl-3-cyclohexene-1-carboxylic acid to form a mixture. The mixture can be heated from about 80° C. to about 100° C. for about 5 minutes to about 20 minutes with vigorous bubbling of $SO_2$. Cessation of $SO_2$ bubbling marks the completion of the reaction. The reaction mixture is then poured into ice to precipitate solid toluic acid, which can be collected by vacuum filtration to isolate a filtrate. The filtrate can be extracted with ethyl acetate (EtOAc), from 1 to about 5 times, and organic layers are combined, dried over $MgSO_4$, and concentrated to form a toluic acid concentrate. The concentrate can be dissolved in EtOAc and filtered through a plug of silica gel to isolate a EtOAc filtrate, followed by washing of the silica gel with EtOAc. In another embodiment, the concentrate is distilled through silica gel, such as in a Kugelrohr distillation procedure. The EtOAc filtrate can be concentrated and recrystallized to afford purified toluic acid.

In exemplary embodiments, the aromatization reaction can involve a vapor phase catalytic dehydrogenation of the para and meta cycloaddition products to form para-toluic acid and meta-toluic acid. Catalysts used in the aromatization reaction include such catalysts that are known in the art for use in catalytic dehydrogenation or catalytic oxidation reactions. Catalysts for use in the aromatization reaction, include, but are not limited to, chromium, molybdenum, iridium, rhodium, ruthenium, nickel, palladium, platinum, vanadium, iron, and manganese. In some embodiments, the catalyst is nickel, platinum or palladium. In exemplary embodiments, the aromatization reaction is catalyzed by a catalyst on a substrate. The substrate can be carbon, silica, alumina, titania, or zirconia. In a preferred embodiment, the catalyst is a Pd(0) on carbon (Pd/C) catalyst. For example, a Pd/C catalyst can be added to one or both of 4-methyl-3- cyclohexene-1-carboxylic acid and 3-methyl-3-cyclohexene-1-carboxylic acid to form a suspension. For example, the suspension can be refluxed for about 3 hours to about 8 hours under air, and then filtered through Celite®, commercialized by Sigma-Aldrich Co. (St. Louis, Mo.), to produce a filtrate. Concentrating the filtrate results in formation toluic acid residue. The dehydrogenation may be conducted at temperatures ranging from about 35° C. to about 500° C., or from about 100° C. to about 400° C. at from about 1 mm to about 750 mm of pressure. In one embodiment, a para cycloaddition product is distilled at from about 50 mm to about 100 mm and from about 100° C. to about 300° C. through Pd on C dispersed in macroporous silica gel. In another embodiment, a homogenous oxidation of para cycloaddition product is performed in mesitylene at from about 75° C. to about 150° C. under $O_2$ catalyzed by Pd(triflate)2, unliganded or liganded with 2-dimethylaminopyridine. In yet another embodiment, a vapor phase dehydrogenation of a 2.5:1 mixture of para:meta product resulting from an uncatalyzed cycloaddition is performed using Pd(0) on C.

In other embodiments, Pd (II) trifluoroacetic acid (Pd (TFA)2), p-toluenesulfonic acid, mesitylene, and 2-(dimethylamino)pyridine are added to one or both of 4-methyl-3-cyclohexene-1-carboxylic acid and 3-methyl-3-cyclohexene-1-carboxylic acid to form a mixture. The mixture can be sparged with 02(g) for about 10 minutes to about 20 minutes, and then heated to from about 80° C. to about 100° C. for about 36 hours to about 54 hours. The mixture can then be filtered to form a filtrate, and the filtrate can be concentrated to toluic acid residue.

In exemplary embodiments, the aromatization reaction is conducted in the presence of sulfuric acid. In exemplary embodiments, the aromatization reaction is performed in acetic anhydride solvent. In exemplary embodiments, the aromatization reaction is conducted in the presence of a catalyst, optionally selected from the group consisting of chromium, molybdenum, iridium, rhodium, ruthenium, nickel, palladium, platinum, vanadium, iron and manganese.

(3) Oxidation Step

In exemplary embodiments, the oxidation of the product of the aromatization reaction, may be carried out by any means necessary or known to those of skill in the art. With reference to FIG. 1, the oxidation reaction is performed to oxidize p- and m-toluic acid to form terephthalic acid and isophthalic acid. In exemplary embodiments, an Amoco Mid-Century oxidation is conducted. Commercially, such oxidation methods are used to convert p-xylene into terephthalic acid. In the present methods, a Co(OAc)$_2$/Mn (OAc)$_2$ catalyst in acetic acid solvent using air as the oxidant and an alkyl halide as a radical chain carrier may be used under high pressure reaction conditions.

In the oxidation reaction, N-hydroxyimides can be used in the presence of metallic salts, to avoid elevated temperatures. Preferred N-hydroxyimides include N-hydroxyphthalimide (NHPI), N-hydroxysuccinimide (NHSI), N-hydroxymaleimide (NHMI), N-hydroxy-1,8-naphthalimide (NHNI), and carbonic acid tert-butyl phthalimido ester (CATPE). Non-limiting examples of metallic salts include Co(II) acetate tetrahydrate, and Mn(OAc)$_2$.

For example, N-hydroxysuccinimide can be used to enable the oxidation of p-toluic acid 5 catalyzed by Co(OAc)$_2$/Mn(OAc)$_2$ in acetic acid solvent to proceed under 1 atm 02 at 100° C. and affords terephthalic acid (94%) and 4-formylbenzoic acid (1%) with 1% unreacted p-toluic acid. Oxidation of m-toluic acid leads to isophthalic acid 8 in 88% yield. p-Toluic acid and m-toluic acid are significantly more reactive than p-xylene under identical reaction conditions. p-Xylene oxidation leads to terephthalic acid (69%), 4-formylbenzoic acid (3%), and p-toluic acid 5 (5%).

In various embodiments, toluic acid, an N-hydroxyimide, at least one metallic salt and glacial acetic acid are mixed together in a reactor to form a mixture. The mixture is purged under $N_2$(g) or $O_2$(g) with stirring and heat is applied to from about 80° C. to about 100° C. Pure $O_2$ is added to the reactor and the mixture is incubated for from about 12 to about 36 hours. Upon completion of the reaction, solid terephthalic acid and/or isophthalic acid products and mother liquor are separated by filtration.

Substituted Aromatics

As described above, the route from bio-isoprene to bio-terephthalic acid exploits a cycloaddition reaction, which is one of the most versatile routes leading to substituted aromatics. Therefore, reaction of the diene isoprene with dienophiles other than acrylic acid provides a route to substituted terephthalates. For example, in various embodiments, bio-based isoprene is reacted with bio-based cinnamic acid to lead to bio-based phenylterephthalic acid, which is a substituted terephthalate additive that imparts unique properties to liquid crystalline polymers. In another embodiment, bio-based isoprene is reacted with bio-based fumaric or maleic acids to lead to trimellitic acid, which in its esterified form, is used as a high performance plasticizer in wire and cable insulation. Similarly, reaction of isoprene with dienophiles other than acrylic acid leads to substituted isophthalates.

Production of PET or Bio-PET

In exemplary embodiments, the terephthalic acid and isophthalic acid made by the methods according to the embodiments described herein may be polymerized with ethylene glycol to yield poly(ethylene terephthalate) (PET). PET may be used, for example, in making fibers, packaging, such as food and beverage containers and bottles. In some embodiments, methods comprise reacting bio-isoprene with a substituted bio-alkene, so as to make substituted terephthalates and isophthalates. Such materials may be used, for example, as performance-enhancing additives in polyester applications.

By starting with one or both of bio-isoprene and bio-acrylic acid, PET can be synthesized in whole or in part from renewable feedstocks. In some embodiments, PET may be made using bio-terephthalic acid with petroleum-based isophthalic acid. Alternatively, PET may be made using petroleum based terephthalic acid with bio-isophthalic acid.

Where the acrylic acid is bio-acrylic acid and the isoprene is bio-isoprene, the scheme results in the synthesis of bio-terephthalic acid, bio-isophthalic acid, or mixtures thereof. Bio-isophthalic acid and bio-terephthalic acid can react with ethylene glycol to generate bio-PET, which can be used in the manufacture of plastic for use in, for example, plastic packaging or fibers. Where the ethylene glycol is bio-ethylene glycol, PET can be generated with 100% of its carbon content derived from renewable feedstocks.

In exemplary embodiments, the bio-terephthalic acid and/or bio-isophthalic acid produced by the methods described herein can be reacted with ethylene glycol to prepare bio-poly(ethylene terephthalate) (also referred to as "bio-PET").

In exemplary embodiments, a method of preparing PET is provided, the method comprising:

(a) reacting isoprene with acrylic acid in the presence of one or more catalysts of Formula I or Formula II to produce 4-methyl-3-cyclohexene-1-carboxylic acid and 3-methyl-3-cyclohexene-1-carboxylic acid;

(b) performing an aromatization reactions on the 4-methyl-3-cyclohexene-1-carboxylic acid and the 3-methyl-3-cyclohexene-1-carboxylic acid to produce bio-para-toluic acid and bio-meta-toluic acid;

(c) performing an oxidation reaction on the para-toluic acid and the meta-toluic acid to form terephthalic acid and isophthalic acid; and (d) polymerizing the terephthalic acid and the isophthalic acid with ethylene glycol to produce PET.

In exemplary embodiments, one or both of the isoprene and acrylic acid are bio-based, so as to produce bio-terephthalic acid (bio-TA) and isophthalic acid (bio-IA), and thereby produce bio-PET. In exemplary embodiments, the terephthalic acid and isophthalic acid are produced at a terephthalic acid: isophthalic acid ratio of from about 90:10 to about 99:1, such as a ratio of about 97:3 or about 95:5. In some embodiments, the PET made by the process comprises cis/trans cyclohexane carboxylic acid.

Methods of Producing Preforms and Articles

The bio-TA, bio-IA and/or bio-PET polymer formed according to the method of the present invention can be used to form a bio-PET resin.

The bio-based PET polymer or resin may be partially or fully bio-based. In one embodiment, the bio-based PET comprises at least one component selected from bio-ethylene glycol (bio-EG), bio-TA, bio-IA or combinations thereof. In one embodiment, the bio-PET comprises bio-TA. In another embodiment, the bio-PET comprises bio-IA. In yet another embodiment, the bio-PET comprises bio-TA and bio-IA. In exemplary embodiments, the bio-PET is totally bio-based.

In one aspect, the present invention is a method of making preforms and articles using the disclosed bio-PET resins disclosed herein. Generally, such preforms and articles are made by forming the above described PET resin into the desired article by conventional methods In one embodiment, the present invention is a method of making a bio-based PET preform, using the disclosed bio-based PET.

Preforms are used in the injection stretch blow molding of plastic containers. A preform is generally made by injection molding a plastic resin.

In exemplary embodiments, the present invention is a method of providing a bio-based PET preform, comprising (i) providing the bio-based PET in a suitable form (e.g., a pellet); (ii) heating the bio-based PET to provide an amorphous bio-based PET melt; (iii) injecting the amorphous bio-based PET into a mold, to provide a bio-based PET preform.

The preform is then stretch blow molded to provide a bio-based PET container. The preform may be used in a single step process or a two-step process, the latter known as reheat injection blow molding. As would be understood by one of skill in the art, the two-step process differs from the single-step process in that the two-step process involves obtaining a preform previously injected molded and cooled to an appropriate storage temperature. In contrast, the one-step process involves stretch blow molding a preform that remains, as a result of injection molding, at a temperature suitable for stretch blow molding.

In one embodiment, the present invention is a method of making a bio-based PET container, using the disclosed copolymer. Suitable methods include blow molding, and more particularly, extrusion blow molding, injection blow molding and injection stretch blow molding. In exemplary embodiments, the container is produced by compression molding.

In one embodiment, the method involves processing the bio-based PET by extrusion blow molding to provide an article, such as a container.

In extrusion blow molding, a specified length of a hollow melt tub (parison) is extruded, clamped in a mold, inflated and cooled against the mold wall, then ejected. Extrusion blow molding may be continuous or intermittent, and there any many variation on the method. To be suitable for use in extrusion blow molding, a polymer composition must exhibit adequate melt strength. Specifically, the polymer composition must exhibit a minimum level of melt strength to maintain parison shape during processing. If the polymer composition lacks sufficient melt strength, the parison will elongate and sag, making inflation and control of container wall thickness difficult.

In exemplary embodiments, the present invention is a method of extrusion blow molding, comprising (i) extruding a hollow tube (parison) of molten resin of an exemplary bio-based PET until a desired length is achieved; (ii) cutting the tube of molten resin; (iii) clamping the tube into a mold having a shape of the container to be produced; (iv) injecting air; and (v) cooling the mold. The particular method of extrusion blow molding is not intended to be limiting, as would be understood by one of skill in the art. In exemplary embodiments, the extrusion blow molding method is continuous.

The bio-based PET disclosed herein can also be processed to produce a bio-based PET article by injection blow molding. With injection blow molding, the hot plastic material is first injected into a cavity where it encircles the blow stem, which is used to create the neck and establish the gram weight. The injected material is then carried to the next station on the machine, where it is blown up into the finished container as in the extrusion blow molding process above. Injection blow molding is generally suitable for smaller containers but not suitable for handleware.

The bio-based PET disclosed herein can also be processed to produce a bio-based PET article by injection stretch blow molding As would be recognized by one of ordinary skill in the art, stretch blow molded plastic containers are manufactured by first preparing an injection molded preform from plastic resin. There are two processes for stretch blow molding containers-single step and two-step.

In one process (single step), the machinery involved injection molds a preform, which is then transferred within the machine to another station where it is blown and then ejected from the machine. This type of machinery is generally called injection stretch blow molding (ISBM) and usually requires large runs.

Thus, in exemplary embodiments, the present invention is a method of producing a bio-based PET container; comprising i) providing the bio-based PET in a suitable form (e.g., a pellet); (ii) heating the bio-based PET to provide an amorphous melt; (iii) injecting the amorphous melt into a mold, to provide a preform; (iv) biaxially stretching the preform by means of a stretch rod and pressurized air, thereby producing a bio-based PET container.

In the other process, a preform has been injection molded previously then cooled. The preform is then place into a machine which reheats it so that it can be blown.

Thus, in exemplary embodiments, the present invention is a method of producing a bio-based PET container, comprising (i) providing a preform comprising the bio-based PET; (ii) heating the preform to a temperature suitable for stretching; and (iii) biaxially stretching the preform by means of a stretch rod and pressurized air, thereby producing a bio-based PET container.

Other suitable methods for processing the bio-PET disclosed herein include but are not limited to compaction plus sintering laminating, reaction injection molding, matched mold, matrix molding, plastic molding, pressure plug assist molding, rotational molding (or rotomolding), transfer molding, thermoforming, vacuum forming, vacuum plug assist molding Preforms and Articles The bio-based TA, IA and/or PET disclosed herein are of value in all forms of application where currently TA, IA and/or PET and similar polyesters or polymers are used, for example in fiber, film and packaging materials.

In exemplary embodiments, the bio-based PET may be used a thermoplastic resin for molding and molded into a desired shape to obtain a molded product. The molding method is not particularly limited. Exemplary molding methods include but are not limited to compression molding, extrusion molding, blow molding or injection molding.

In exemplary embodiments, the bio-based PET may be used with or may contain a required amount of an additive such as a colorant, dye, pigment, UV absorbing compound, antioxidant, plasticizer, softener, IR absorbers, flame retardant, an internal releasing agent, stabilizer, or any of various fillers known in the art.

In exemplary embodiments, a molded article molded with an exemplary polymer or a resin formulation comprising the bio-based TA, IA or PET is provided.

In exemplary embodiments, the bio-based TA, IA or PET may be used in fiber, film or packaging materials where high barrier properties are desirable, for example in packaging or containers for carbonated beverages or oxygen sensitive food. In exemplary embodiments, the bio-based TA, IA or PET may be used in fiber, film or packaging materials where to protect oxygen sensitive substances, beverages or materials, for example in packaging or containers for fruit juices, vitamin waters, beer, and wine. In exemplary embodiments, the protection of oxygen sensitive substances or materials can be achieved by using the bio-based TA, IA or PET and without the use of oxygen scavengers or multilayer film technology.

In exemplary embodiments, the present invention is an article made from the bio-based TA, IA or PET disclosed herein. In exemplary embodiments, the article is a container, such as a bottle, can, pouch, carton, form-filled seal pack, bag-in-a-box, and primary packaging wraps. The bio-PET article can also be a component of packaging, for example, a barrier liner for a closure or a finish design part for a closure, frangible seal, heat seal or recloseable seal.

In exemplary embodiments, the bio-PET article is a bottle, such as a beverage bottle. In a particular embodiment, the bio-PET article is a bottle having a volume of about 500 mL or less. In another particular embodiment, the bio-PET article is a bottle having a volume of about 400 mL, about 350 mL, about 300 mL, about 250 mL, about 200 mL or less.

In another embodiment, the bio-PET article is a film, such as an architectural film, construction film, consumer film, labels, heat-shrinkable monolayer film or heat-shrinkable multilayer film. The bio-PET article can also be an article comprising or containing a film, where the article is primary packaging: plastic wraps, case-ready films, sandwich bags, freezer bags, chip bags, vacuum-sealed bags, bags for bag-in-a-box containers, heat-shrink wraps, microwavable bags, microwavable wraps and foamed films. The bio-PET article can also be an article that comprises a film, where the article is secondary packaging: sleeves for aggregating containers, sealed bags for aggregating containers, and blister pack films for encasing prior-wrapped foods and drugs.

In another embodiment, the bio-PET article is an adhesive, such as a reactive or non-reactive adhesive. The adhesive may be, for example, drying, pressure-sensitive adhesive, contact adhesive, or a hot-melt adhesive.

In a further embodiment, the bio-PET article is a bag. In exemplary embodiments, the bio-PET article is a grocery bag, trash bag, laundry bags, dry-cleaning cover, shopping bag, or promotional bag.

In yet another embodiment, the bio-PET article is a wrapper, such as a wrapper for items in storage, sealed wrappers for products on sale, or a resealable wrappers.

In a further embodiment, the bio-PET article may be a coating, for example, a coating on an internal surface of a bottle, can, pouch, carton, form-filled seal packs, bag-in-a-box, or as a coating on a product-facing surface of a primary packaging wrap In a still further embodiment, the bio-PET article is dinnerware or an eating utensil.

In yet another embodiment, the bio-PET article is a molded part, for example for a vending machine.

In exemplary embodiments, the bio-PET article is a heat-tolerant article such as (i) bowls or cups for holding coffee, tea, cocoa, and soup; (ii) hot fill cans, pouches and cartons; or (iii) microwavable packaging for food and beverages.

In exemplary embodiments, the bio-PET article is used to contain a beverage or food that is hot-filled. For example, a beverage or food that is hot-filled into the containers and sealed so as to eliminate microbial contamination.

In exemplary embodiments, the bio-PET article is a hot-fill container for containing a food or beverage, wherein the article is designed to manage the shrinkage during cooling. For example, the article is design to accommodate shrinkage during cooling by means of one or more concave vacuum panel areas into the sidewall of the container that are designed to deflect inwardly as the product cools.

In exemplary embodiments, the bio-PET article is a hot-fill container for containing a high acid beverage or food (pH less than about 4.6). In a particular embodiment, the article is a hot-fill container for containing juice, vegetable juice, nectar, tea or the like.

In exemplary embodiments, the bio-PET article is a form of packaging selected from the group consisting of: meal trays, meal covers, clamshells, plates, platters, bowls, saucers, mugs, drink cups, custard cups, lids, forks, knives, spoons, chop sticks, combination utensils, skewer, tongs, toothpicks, straws, seasoning dispensers, pitchers, gravy boats and casserole dishes.

In exemplary embodiments, when the bio-PET disclosed herein is used for packaging, for example for bottles, then it may also be desired to incorporate other improvements into the packaging, such as the use of a bio-based closure. Exemplary materials for closures, include the use of poly (hydroxyl butyrate-co-valerate) (PBHV), other poly(hydroxyalkanoates), poly(lactic acid), new bio-based materials such as poly(butylene succinate), bio-based polyethylene, biobased polypropylene, polylactic acid, modified starches, and the blends above. The label may be of clear or colored material, and may be attached with adhesives or used as a shrink sleeve. Either the adhesive or shrink sleeve could be made, for example, from bio-based materials including but not limited to poly(lactic) acid based materials. In exemplary embodiments, a dye may be included in the copolymer or in a resin formulation comprising the copolymer, in order to give a distinctive look to the packaging or to protect the materials from light. For example, a dark amber or green bottle may be used in the packaging of light-sensitive substances or beverages. For colorless or substantially colorless bottles, a suitable amount of a bluing agent can be used to help mask the small amount of yellow color which is found in many polymeric resins. For printing directly onto the polymer product, various surface treatments, such as corona treatment, may be used. If used as a packaging material, the polymer product may be subject to sterilization using any of the techniques known in the art, including but not limited to ozone treatment, UV treatment e-beam treatment, chemical surface contact treatment (aseptic), and the like.

Terms

When describing the compounds for use in the disclosure, the terms used are to be construed in accordance with the following definitions, unless a context dictates otherwise As used herein, "alkyl" means a noncyclic straight chain or branched, unsaturated or saturated hydrocarbon such as those containing from 1 to 10 carbon atoms, while the term "lower alkyl" has the same meaning as alkyl but contains from 1 to 6 carbon atoms. The term "higher alkyl" has the same meaning as alkyl but contains from 7 to 20 carbon atoms. In certain embodiments, the disclosure contemplates that alkyl refers to lower alkyl or higher alkyl.

Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, $-NR^aR^b$, $-NR^aC(=O)R^b$, $-NR^aC(=O)NR^aNR^b$, $-NR^aC(=O)OR^b$, $-NR^aSO_2R^b$, $-C(=O)R^a$, $-C(=O)$ $OR^a$, $-C(=O)NR^aR^b$, $-OC(=O)NR^aRb$, $-OR^a$, $-SR^a$, $-SOR^a$, $-S(=O)_2R^a$, $-OS(=O)_2R^a$ and $-S(=O)_2OR^a$. $R^a$ and $R^b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The following examples are presented for illustrative purposes only, and are not intended to be limiting.

EXAMPLES

General $^1$H NMR spectra were recorded on a 500 MHz spectrometer. Chemical shifts for $^1$H NMR spectra are reported (in parts per million) relative to CDCl$_3$ (δ=7.26 ppm) unless stated otherwise. GC analysis was performed on an Agilent 6890N chromatograph equipped with an autosampler. Reagents were purchased from Sigma-Aldrich and used without further purification. Boron trichloride (BCl$_3$) was a 1 M solution in heptane. Borane (BH$_3$) was a 1 M solution in tetrahydrofuran (THF). The cycloadditions were performed in a 3 mL vial or 40 mL pressure vessel (Chemglass Inc., maximum pressure limit=13.8 bar) with a screw cap (15 mm PTFE bushing with Viton® O-ring). Reaction products were purified by column chromatography on silica gel (40-63 μm) unless stated otherwise.

Example 1. Preparation and Characterization of BOBPh$_4$

To a solution of 2-aminoethyl diphenylborinate (1.27 g, 5.6 mmol) in a 20 mL vial with 4 mL of MeOH/acetone (1:1, v/v) was added 15 mL of 1 M HCl. The reaction mixture was stirred at ambient temperature for 1 h, then dissolved in EtOAc (50 mL) and finally extracted with brine (3×, 20 mL). After drying and concentration of the organic layer, the obtained solid diphenylborinic acid was heated at 80° C. for 2 h under vacuum to afford diphenylborinic anhydride as a light yellow solid (746 mg, 76%). $^1$H NMR (500 MHz, CDCl$_3$) δ=7.90 (d, J=6.8 Hz, 8H), 7.52 (dd, J=7.3 Hz, 7.3 Hz, 4H), 7.44 (dd, J=7.3 Hz, 7.3 Hz, 8H). $^{13}$C NMR (125 MHz, CDCl$_3$) δ=135.8, 131.3, 127.9.

$^1$H NMR spectra for the product before and after drying is shown in FIGS. 1a and 1b.

Example 2. Preparation and Characterization of BOB(OAc)$_4$

To a 25 mL two-neck round bottom flask was added boric acid (1.0 g, 16.1 mmol) and acetic anhydride (6.0 g, 58 mmol). The cloudy crude was heated to 110° C. under nitrogen for 2 h, which afforded a clear, colorless solution. After cooling to 0° C. with an ice bath, a white solid precipitated out of the clear solution. The liquid was removed by pipet and the solid was washed with diethyl ether (3×, 6 mL). After drying under vacuum, 1.85 g (84%) of product was obtained as a white solid. $^1$H NMR (500 MHz, CDCl$_3$) δ=2.23 (s, 12H. $^{13}$C NMR (125 MHz, CDCl$_3$) δ=22.5, 178.2. $^{11}$B NMR (160 MHz, CDCl$_3$) δ=2.11 (s).

Figures 2A, 2B:
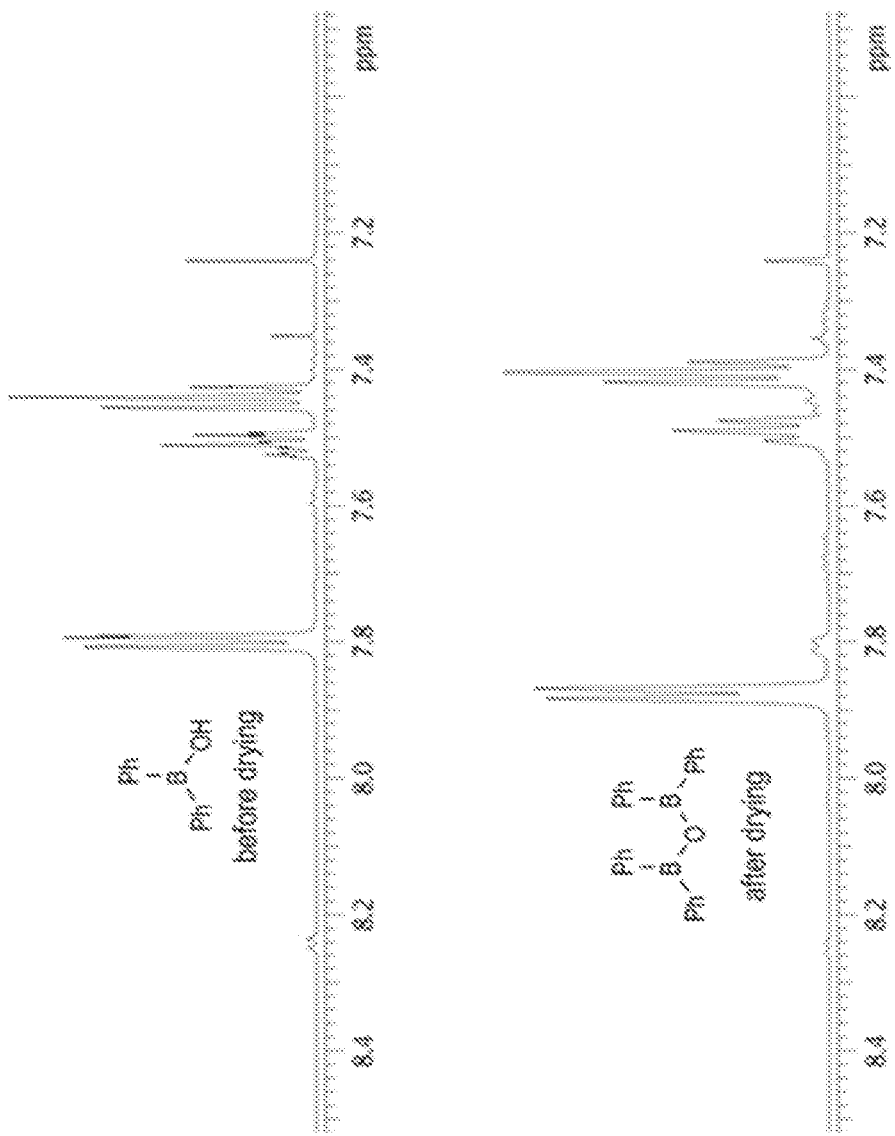
FIGS. 2a and 2b show $^1$H NMR spectra for diphenylborinic acid (FIG. 4a) and diphenylborinic anhydride (FIG. 4b), both in CDCl$_3$.
Figure 3:
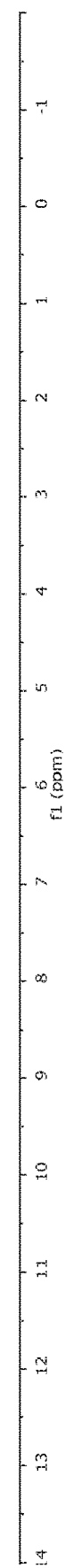
FIGS. 3, 4 and 5, respectively, show $^1$H, 13C and $^{11}$B NMR spectra for tetraacetyl diborate, all in CDCl$_3$.
Figure 4:
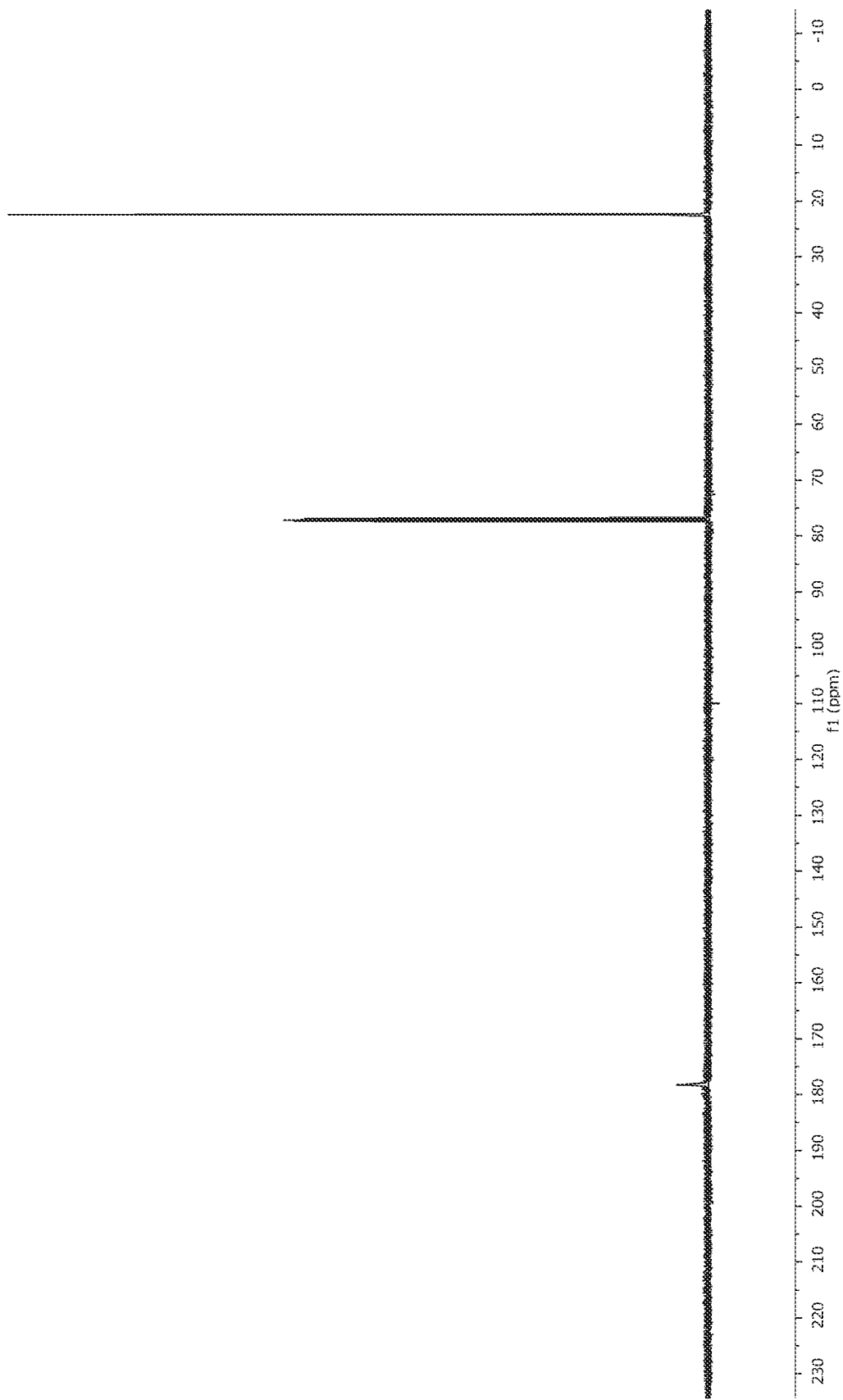

$^1$H, $^{13}$C and $^{11}$B NMR spectra for the product are shown in FIGS. 2, 3, and 4, respectively.

Example 3. Cycloaddition Reactions of Unesterified Acrylic Acids Catalyzed by Exemplary Catalysts In this study, exemplary catalysts including BCl$_3$ 1a, Cl$_2$BOTFAc 2a (trifluoroacetoxydichloroborane), Cl$_2$BOAc 3a (acetoxydichloro-borane), BOB(OAc)$_4$ (tetraacetyl diborate) 8a and BOBPh$_4$ (diphenylborinic anhydride) 9a were examined as catalysts for cycloadditions of unesterified acrylic acids. Comparative catalysts known to catalyze cycloadditions of unesterified acrylic acids, including BH$_3$ 4a, o-bromophenylboronic acid 5a and TiCl$_4$ 7a, were also examined. (For examples of cycloaddition reactions involving the comparative catalysts, see: (a) Furata, K., et al.; *J. Am. Chem. Soc.* 1988, 110, 6254-6255; (b) Al-Zoubi, R. M., et al.; *Angew. Chem. Int. Ed.* 2008, 47, 2876-2879; (c) Hall, D., et al.; U.S. Pat. No. 8,822,720; (d) Zheng, H. and Hall, D. G. *Aldrichimica Acta* 2014, 47, 41-51; (e) Miles, W. H., et al.; *Synth. Commun.* 2013, 43, 1980; (f) Robinson, R. and Fray, G. I. GB Patent No. 835840; (g) Robinson, R. and Fray, G. I.; U.S. Pat. No. 306,724; (h) Takenaka, S., et al. J P Patent No. 54157546 A; and (i) Miller, K. K., et al.; *ACS Sustainable Chem. Eng.* 2014, 2, 2053-2056).

Generally, all reactions were performed with 5 mmol of acrylic acid and 5 mmol of isoprene with about 2 mol % of catalysts (about 10 mol % BOBPh$_4$ was used) in a 3 mL vial at ambient temperature, substantially in the absence of a solvent, except where a minimum amount of solvent was transferred into the reaction with the catalyst (BCl$_3$ was a 1 M solution in heptane and BH$_3$ was a 1 M solution in THF). Exemplary experimental protocols for selected cycloaddition reactions are provided below. Similar protocols were carried out for the other cycloaddition reactions, and it will be understood to those of ordinary skill in the art how to carry out such reactions.

A. BOB(OAc)$_4$ Catalyzed Cycloaddition of Acrylic Acid and Isoprene

To a 3 mL vial containing tetraacetyl diborate (27.4 mg, 0.1 mmol) under air was added acrylic acid (360 mg, 5 mmol). The mixture was stirred at ambient temperature for 1 min, followed by addition of isoprene (0.55 mL, 5.5 mmol). After the completion of the reaction, the crude was loaded directly onto a flash column. Chromatographic purification (EtOAc:hexanes:AcOH=5:100:1) gave 673 mg (96%, para/meta=95:5) of a white solid.

B. BOBPh$_4$ Catalyzed Cycloaddition of Acrylic Acid and Isoprene

To a 3 mL vial containing diphenylborinic anhydride (173 mg, 0.5 mmol) under air was added acrylic acid (360 mg, 5 mmol). The mixture was stirred at ambient temperature for 1 min, followed by addition of isoprene (0.55 mL, 5.5 mmol). After the completion of the reaction, the crude was loaded directly onto a flash column and purified using EtOAc:hexanes:AcOH=5:100:1 as mobile phase.

C. Cl$_2$BOTFAc Catalyzed Cycloaddition of Acrylic Acid and Isoprene

To a 40 mL pressure vessel under air was added silver trifluoroacetate (22 mg, 0.1 mmol), acrylic acid (360 mg, 5 mmol) and isoprene (0.55 mL, 5.5 mmol). The mixture was stirred at ambient temperature for 1 min, followed by addition of BCl$_3$ (100 µL, 0.1 mmol). The vessel was then sealed and the reaction stirred at ambient temperature for 22 h. After the reaction was completed, the crude was loaded directly onto a flash column and purified using EtOAc:hexanes:AcOH=5:100:1 as mobile phase.

D. Cl$_2$BOAc Catalyzed Cycloaddition of Acrylic Acid and Isoprene

To a 40 mL pressure vessel under air was added silver acetate (16.7 mg, 0.1 mmol), acrylic acid (360 mg, 5 mmol) and isoprene (0.55 mL, 5.5 mmol). The mixture was stirred at ambient temperature for 1 min, followed by addition of BCl$_3$ (100 µL, 0.1 mmol). The vessel was then sealed and the reaction stirred at ambient temperature for 22 h. After the reaction was completed, the crude was loaded directly onto a flash column. Chromatographic purification (EtOAc:hexanes:AcOH=5:100:1) gave 689 mg (98%, para/meta=96:4) of a white solid.

E. Comparative: BCl$_3$ Catalyzed Cycloaddition of Acrylic Acid and Isoprene

To a 40 mL pressure vessel under air was added acrylic acid (360 mg, 5 mmol) and isoprene (0.55 mL, 5.5 mmol). The mixture was stirred at ambient temperature for 1 min, followed by adding BCl$_3$ (100 µL, 0.1 mmol). The vessel was then sealed and the reaction stirred at ambient temperature for 22 h. After the reaction was completed, the crude was loaded directly onto a flash column and purified using EtOAc:hexanes:AcOH=5:100:1 as mobile phase.

F. Comparative: BH$_3$ Catalyzed Cycloaddition of Acrylic Acid and Isoprene

To a 3 mL vial containing acrylic acid (360 mg, 5 mmol) under air was added BH$_3$ (0.1 mL, 1.0 M in THF). The mixture was stirred at rt for 1 min, followed by addition of isoprene (0.55 mL, 5.5 mmol). After the completion of the reaction, the crude was directly analyzed by NMR.

G. Comparative: TiCl$_4$ Catalyzed Cycloaddition of Acrylic Acid and Isoprene

To a 3 mL vial containing acrylic acid (360 mg, 5 mmol) under air was added TiCl$_4$ (11 µL, 0.1 mmol). The mixture was stirred at rt for 1 min, followed by addition of isoprene (0.55 mL, 5.5 mmol). After the completion of the reaction, the crude was directly analyzed by NMR.

The product distribution of each cycloaddition reaction is shown below in Table 1. The rates for the cycloaddition reactions involving acrylic acid and isoprene were also investigated and the results are shown in FIG. 1. In order to assess reaction rates, after the designated time (10 min, 20 min, 40 min, 1 h, 2 h, and 3 h), an aliquot was withdrawn for an NMR determination of percent yield.

TABLE 1

Cycloadditions of Unesterified Acrylic Acids Catalyzed by BOB(OAc)$_4$, (Ph$_2$B)$_2$O, BCl$_3$, BH$_3$, and TiCl$_4$.

| Exp. | Substrates mol:mol, [catalyst], ° C. | Product(s) | Yield BOB(OAc)$_4$ [a,e] | BOBPh$_4$ [a,e] | BCl$_3$ [a,f] | Cl$_2$BOTFAc [a] | BH$_3$ [b,g] | TiCl$_4$ [b,e] |
|---|---|---|---|---|---|---|---|---|
| 1[a] | 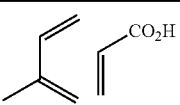 1:1, 2 mol %, rt | 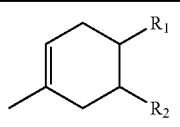 para: R$_1$ = CO$_2$H, R$_2$ = H meta: R$_1$ = H, R$_2$ = CO$_2$H 3-chloropropionic acid | 91% 5% [b] 0% | [d] 93% [d] 3% [b,d] 0% | 91% 5% [b] 4% | 97% 2% [b] trace | 95% 5% 0% | 89% 4% 0% |

TABLE 1-continued

Cycloadditions of Unesterified Acrylic Acids Catalyzed by BOB(OAc)$_4$, (Ph$_2$B)$_2$O, BCl$_3$, BH$_3$, and TiCl$_4$.

| Exp. | Substrates mol:mol, [catalyst], °C. | Product(s) | Yield BOB(OAc)$_4$ [a,e] | BOBPh$_4$ [a,e] | BCl$_3$ [a,f] | Cl$_2$BOTFAc [a] | BH$_3$ [b,g] | TiCl$_4$ [b,e] |
|---|---|---|---|---|---|---|---|---|
| 2 | 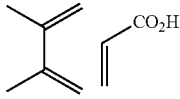<br>2:1, 2 mol %, rt | 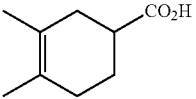<br>3-chloropropionic acid | 99%<br>[b] 0% | [d] 99%<br>[b,d] 0% | 99%<br>[b] trace | 98%<br>[b] trace | 96%<br>0% | 93%<br>0% |
| 3 | 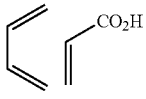<br>2:1, 10 mol %, rt | 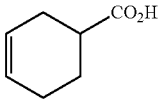<br>3-chloropropionic acid | 99%<br>[b] 0% | 53%<br>[b] 0% | 75%<br>[b] 26% | 95%<br>[b] 6% | 100%<br>0% | 100%<br>0% |
| 4 | 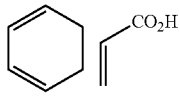<br>2:1, 10 mol %, rt | 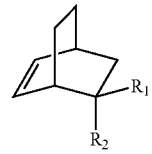<br>endo: R$_1$ = H, R$_2$ = CO$_2$H<br>exo: R$_1$ = CO$_2$H, R$_2$ = H<br>3-chloropropionic acid | 97%<br>0%<br>[b] 0% | 58%<br>0%<br>[b] 0% | 79%<br>0%<br>[b] 26% | [c] 94%<br>[c] 0%<br>[b,c] 2% | 99%<br>0%<br>0% | 93%<br>0%<br>0% |
| 5 | 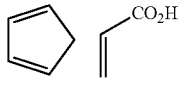<br>2:1, 2 mol %,<br>0° C. | 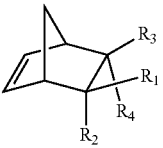<br>endo: R$_1$ = H, R$_2$ = CO$_2$H, R$_3$ = H, R$_4$ = H<br>exo: R$_1$ = CO$_2$H, R$_2$ = H, R$_3$ = H, R$_4$ = H<br>3-chloropropionic acid | 83%<br>12%<br>[b] 0% | [d] 75%<br>[d] 9%<br>[b,d] 0% | 91%<br>9%<br>[b] 0% | 87%<br>11%<br>[b] 0% | 88%<br>12%<br>0% | 83%<br>17%<br>0% |
| 6 | 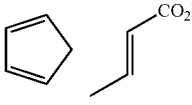<br>2:1, 10 mol %,<br>0° C. | 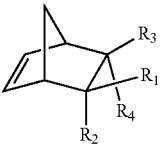<br>endo: R$_1$ = H, R$_2$ = CO$_2$H, R$_3$ = CH$_3$, R$_4$ = H<br>exo: R$_1$ = CO$_2$H, R$_2$ = H, R$_3$ = H, R$_4$ = CH$_3$ | 90%<br>8% | [b] 24% | 58%<br>7% | polymer formation | 66%<br>11% | 0%<br>0% |
| 7[b] | 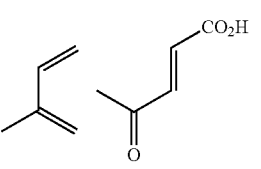<br>10:1, 2 mol %, rt | 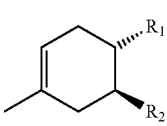<br>para: R$_1$ = CO$_2$H, R$_2$ = C(O)CH$_3$<br>meta: R$_1$ = C(O)CH$_3$, R$_2$ = CO$_2$H | [d] 70%<br>[d] 20% | [b,d] 89% | [d] 62%<br>[d] 31% | polymer formation | 8%<br>8% | 33%<br>67% |

TABLE 1-continued

Cycloadditions of Unesterified Acrylic Acids Catalyzed by BOB(OAc)$_4$, (Ph$_2$B)$_2$O, BCl$_3$, BH$_3$, and TiCl$_4$.

| | | | Yield | | | | | |
|---|---|---|---|---|---|---|---|---|
| Exp. | Substrates mol:mol, [catalyst], °C. | Product(s) | BOB(OAc)$_4$ [a,e] | BOBPh$_4$ [a,e] | BCl$_3$ [a,f] | Cl$_2$BOTFAc [a] | BH$_3$ [b,g] | TiCl$_4$ [b,e] |
| 8[b] | 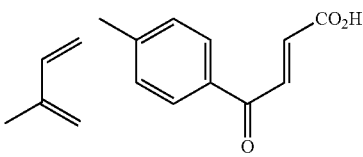<br>10:1, 10 mol %, rt | 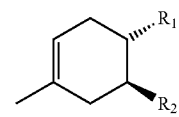<br>para: R$_1$ = CO$_2$H, R$_2$ = C(O)C$_6$H$_4$-4-CH$_3$<br>meta: R$_1$ = C(O)C$_6$H$_4$-4-CH$_3$, R$_2$ = CO$_2$H | 77%<br>22% | 62%<br>36% | 66%<br>26% | 73%<br>26% | 39%<br>20% | 33%<br>67% |

[a] Isolated yield.
[b] $^1$H NMR yield from crude reaction mixture.
[c] 5 mol % catalyst.
[d] 10 mol % catalyst.
[e] solvent-free
[f] heptane [acryl acids] = 0.5-5M
[g] THF [acryl acids] = 0.5-5M.

In addition to the results shown in Table 1, $^1$H NMR yields from crude reactions using o-BrPhB(OH)$_2$ 5a under solvent-free conditions were 66% for Experiment 5 and less than 20% for Experiments 1-4 and 6-8.

Uncatalyzed Cycloaddition of Acrylic Acid and Isoprene

As a further comparative example, uncatalyzed, 95° C. cycloaddition of acrylic acid with isoprene gave a 59% yield of para cycloadduct. Acrylic acid (71.4 g, 0.991 mol) was added to isoprene (77.5 g, 1.14 mol) under N$_2$ in a Parr Series 4575 high pressure reactor interfaced with a Series 4842 temperature controller. The reactor was flushed with N$_2$ and then pressurized to 8.3 bar with N$_2$. Heating the reactor at 95° C. with stirring (100 rpm) for 2 h led to an initial increase in pressure to 13.8 bar followed by a decline in pressure to 9.7 bar. After allowing the reactor to cool, a yellow heterogeneous reaction crude was obtained containing a 59% yield of para cycloadduct and a 20% yield of meta cycloadduct. Crude product was submitted to repeated crystallizations from hexanes to obtain 37.5 g (27% yield) of pure para-cycloadduct.

Cl$_2$BOTFAc 2a increased cycloadduct yield to 97% and lowered 3-chloropropionic acid formation to trace levels (entry 1, Table 1). For all BCl$_3$-catalyzed cycloadditions with significant 3-chloropropionic acid formation, Cl$_2$BOTFAc 2a catalysis substantially reduced this byproduct formation (entry 1, 3 and 4, Table 1).

Cl$_2$BOAc 3a catalyzed the cycloaddition of acrylic acid with isoprene to afford a 94% yield of para cycloadduct, a 4% yield of meta cycloadduct, and trace levels of 3-chloropropionic acid formation.

BOB(OAc)$_4$ 8a catalysis afforded high product yields for all of the cycloadditions (Table 1, entry 1-8) with no polymerization observed using solvent-free conditions. A nearly quantitative yield was obtained with BOB(OAc)$_4$ catalysis irrespective of whether a reactive 2,3-dimethyl-1,3-butadiene (entry 2, Table 1) or unreactive 1,3-butadiene (entry 3, Table 1) was the diene. Notably, in the reaction of crotonic acid with cyclopentadiene (entry 6, Table 1), the 98% yield of cycloadducts using BOB(OAc)$_4$ catalysis contrasted with the absence of cycloadduct using TiCl$_4$ catalysis. While BH$_3$-catalyzed reactions of β-acylacrylic acids with isoprene led to low to modest yields, BOB(OAc)$_4$ catalysis afforded ≥90% yields of cycloadducts (entry 7 and 8, Table 1).

Diphenylborinic anhydride 9a also catalyzed high-yielding cycloaddition reactions (entries 1, 2, 7, 8, Table 1).

Figure 5:
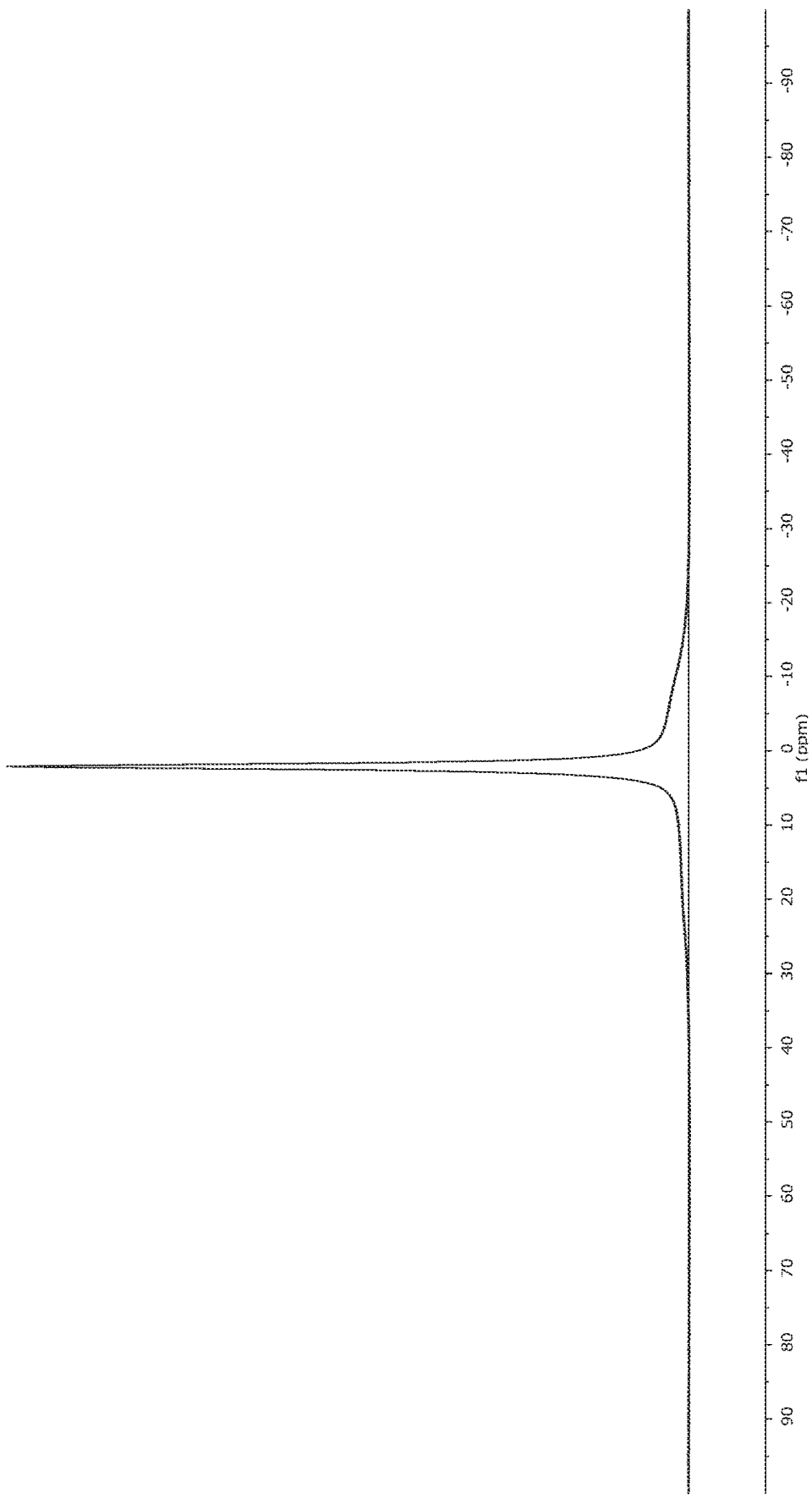
Figure 6:
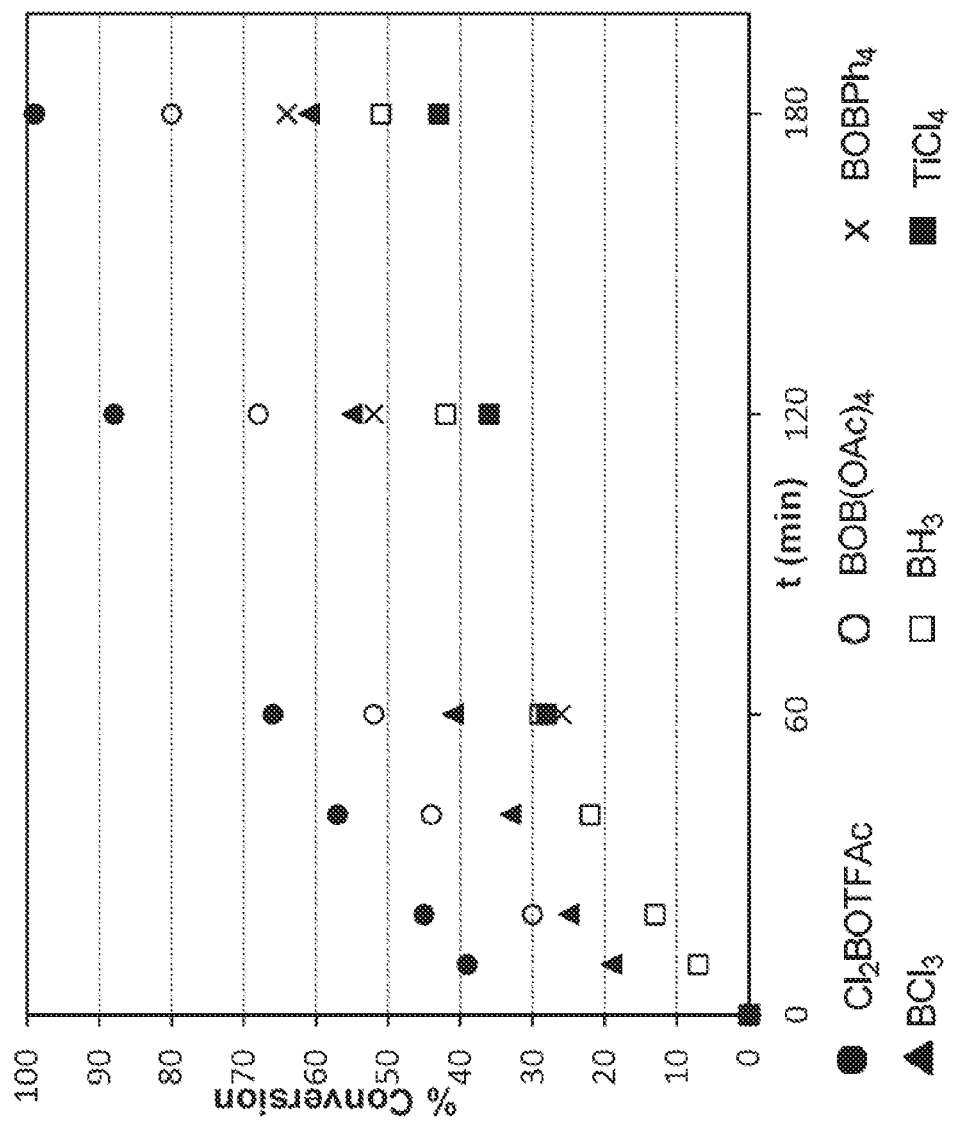
FIG. 6 shows the acrylic acid and isoprene cycloaddition reaction rates for several exemplary and comparative catalysts.

There were significant differences in cycloaddition rates of acrylic acids as a function of the catalyst employed. The cycloaddition of acrylic acid with isoprene (Table 1, entry 1) was used as the basis for comparing catalyzed rates (FIG. 5). The most rapid cycloaddition rate was observed with Cl$_2$BOTFAc followed by BOB(OAc)$_4$ catalysis. The slowest cycloaddition rate was catalyzed by TiCl$_4$ and the next slowest catalyzed by BH$_3$.

Cycloaddition Products Purification and Characterization 4-methyl-3-cyclohexenecarboxylic acid

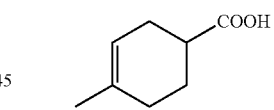

$^1$H NMR (500 MHz, CDCl$_3$) δ=1.63 (s, 3H), 1.70 (m, 1H), 1.92-2.26 (m, 3H), 2.16-2.28 (m, 2H), 2.50 (m, 1H), 5.40 (s, 1H), 11.73 (br s, 1H). $^{13}$C NMR (125 MHz, CDCl$_3$) δ=23.5, 25.2, 27.4, 29.1, 39.0, 119.0, 138.8, 182.5.

3,4-dimethyl-3-cyclohexenecarboxylic acid

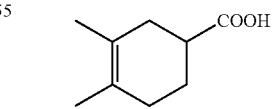

The reaction was performed on 5 mmol scale. Chromatographic purification (EtOAc:hexanes:AcOH=5:100:1) gave 762 mg (99%) of a white solid. $^1$H NMR (500 MHz, CDCl$_3$) δ=1.62 (s, 3H), 1.64 (s, 3H), 1.68 (m, 1H), 1.96-2.10 (m, 3H), 2.12-2.28 (m, 2H), 2.58 (m, 1H), 11.85 (br s, 1H). $^{13}$C NMR (125 MHz, CDCl$_3$) δ=18.8, 19.0, 25.6, 31.0, 33.7, 40.0, 123.7, 125.4, 182.8.

3-cyclohexenecarboxylic acid

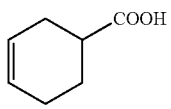

The reaction was performed on 5 mmol scale. Butadiene was first cooled to a liquid in a −78° C. bath. The reaction was set up at −78° C. and warmed up to rt in a 15 mL pressure vessel. Chromatographic purification (EtOAc:hexanes:AcOH=5:100:1) gave 626 mg (99%) of a colorless oil. $^1$H NMR (500 MHz, CDCl$_3$) δ=1.68-1.76 (m, 1H), 2.02-2.18 (m, 3H), 2.22-2.34 (m, 2H), 2.57-2.65 (m, 1H), 5.65-5.73 (m, 2H), 11.98 (br s, 1H). $^{13}$C NMR (125 MHz, CDCl$_3$) δ=24.3, 24.8, 27.1, 39.2, 125.0, 126.7, 182.8.

bicyclo[2.2.2]oct-5-ene-2-carboxylic acid

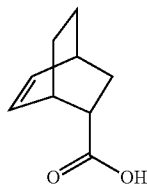 [SMILES: O=C(O)C1CC2C=CC1CC2]

The reaction was performed on 5 mmol scale. Chromatographic purification (EtOAc:hexanes:AcOH=5:100:1) gave 736 mg (97%) of a white solid. $^1$H NMR (500 MHz, CDCl$_3$) δ=1.18-1.32 (m, 2H), 1.43-1.50 (m, 1H), 1.53-1.60 (m, 1H), 1.60-1.68 (m, 1H), 1.70-1.78 (m, 1H), 2.58 (m, 1H), 2.64 (m, 1H), 2.95 (m, 1H), 6.15 (dd, J=6.4 Hz, 6.4 Hz, 1H). 6.30 (dd, J=7.4 Hz, 7.4 Hz, 1H), 11.25 (br s, 1H). $^{13}$C NMR (125 MHz, CDCl$_3$) δ=24.4, 25.4, 29.3, 29.6, 32.4, 42.7, 131.3, 135.2, 182.3.

bicyclo[2.2.1]hept-5-ene-2-carboxylic acid

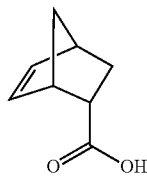

The reaction was performed on 5 mmol scale. Cyclopentadiene was obtained from cracking of dicyclopentadiene at 160° C. Chromatographic purification (EtOAc:hexanes:AcOH=10:100:1) 657 mg (95%) of a colorless oil. Endo-product $^1$H NMR (500 MHz, CDCl$_3$) δ=1.29 (d, J=7.8 Hz, 1H), 1.36-1.48 (m, 2H), 1.93 (m, 1H), 2.94 (s, 1H), 2.98 (dt, J=3.9 Hz, 9.3 Hz, 1H), 3.24 (s, 1H), 6.00 (dd, J=3.0 Hz, 5.4 Hz, 1H), 6.21 (dd, J=3.0 Hz, 5.8 Hz, 1H), 11.60 (br s, 1H). $^{13}$C NMR (125 MHz, CDCl$_3$) δ=29.1, 42.5, 43.3, 45.7, 49.7, 132.5, 137.9, 181.6.

(2-endo,3-exo)-3-methyl-bicyclo[2,2,1]hept-5-ene-2-carboxylic acid

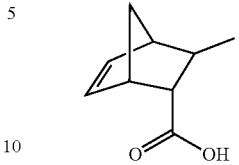

The reaction was performed on 5 mmol scale. Chromatographic purification (EtOAc:hexanes:AcOH=5:100:1) gave 742 mg (98%) of a white solid. Endo-product $^1$H NMR (500 MHz, CDCl$_3$) δ=1.19 (d, J=7.0 Hz, 3H), 1.45 (ddd, J=1.7 Hz, 3.5 Hz, 8.7 Hz, 1H), 1.55 (d, J=8.4 Hz, 1H), 1.83 (m, 1H), 2.42 (dd, J=3.5 Hz, 4.5 Hz, 1H), 2.48 (br s, 1H), 3.14 (br s, 1H), 6.04 (dd, J=2.8 Hz, 5.7 Hz, 1H), 6.28 (dd, J=3.1 Hz, 5.7 Hz, 1H), 11.50 (br s, 1H). $^{13}$C NMR (125 MHz, CDCl$_3$) δ=20.9, 37.9, 45.8, 46.1, 48.8, 52.4, 133.3, 138.9, 181.7.

6-acetyl-4-methylcyclohex-3-enecarboxylic acid

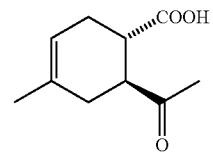

The reaction was performed on 2 mmol scale. Chromatographic purification (EtOAc:hexanes:AcOH=25:100:1) gave 327 mg (90%, para/meta 3.5:1) of a white solid. Para-product $^1$H NMR (500 MHz, CDCl$_3$) δ=1.65 (s, 3H), 1.84-2.16 (m, 2H), 2.21 (s, 3H), 2.26-2.44 (m, 2H), 2.76 (dt, J=5.4 Hz, 10.8 Hz, 1H), 2.94 (dt, J=5.4 Hz, 10.8 Hz, 1H), 5.40 (s, 1H), 11.80 (br s, 1H). $^{13}$C NMR (125 MHz, CDCl$_3$) δ=23.0, 28.2, 29.9, 32.0, 40.7, 48.5, 119.3, 132.1, 181.7, 211.1.

4-methyl-6-(4-methylbenzoyl)cyclohex-3-enecarboxylic acid

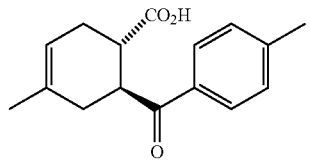

The reaction was performed on 1 mmol scale. Chromatographic purification (EtOAc:hexanes:AcOH=1:6:1%) gave 254 mg (99%, para/meta=3.5:1) of a yellow foam-like solid. Para-product $^1$H NMR (500 MHz, CDCl$_3$) δ=1.63 (s, 3H), 1.95 (m, 1H), 2.15-2.30 (m, 2H), 2.37 (s, 3H), 2.44-2.53 (m, 1H), 3.02 (dt, J=5.5 Hz, 11.1 Hz, 1H), 3.80 (dt, J=5.5 Hz, 11.2 Hz, 1H), 5.43 (br s, 1H), 7.23 (d, J=7.3 Hz, 2H), 7.87 (d, J=8.3 Hz, 2H), 11.75 (br s, 1H). $^{13}$C NMR (125 MHz, CDCl$_3$) δ=21.6, 23.0, 28.5, 33.8, 41.1, 42.8, 119.2, 128.6, 129.3, 132.5, 133.5, 143.9, 181.7, 202.3.

Example 4. Cycloaddition Reactions to Form Indole-3-Propionic Acid Catalyzed by Exemplary Catalysts

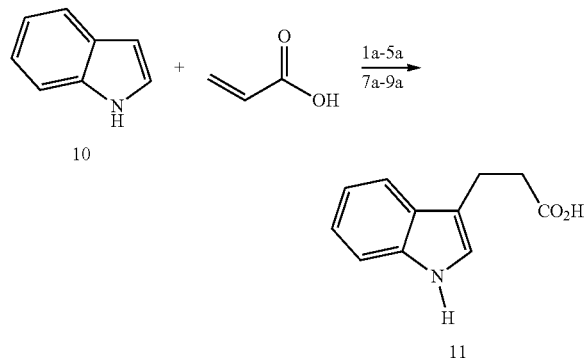

The exemplary and comparative catalysts' reactivity towards alkylation of nucleophilic aromatic cores was tested through the reaction of indole 10 to form indole-3-propionic acid 11 in DCM with acrylic acid.

To a 3 mL vial containing indole (117 mg, 1 mmol) in 1 mL of $CH_2Cl_2$ under air was added acrylic acid (137 μL, 2 mmol). The mixture was stirred at ambient temperature for 1 min, followed by addition of 20 mol % of catalyst. After 16 h of reaction, the crude was loaded directly onto a flash column. Chromatographic purification (EtOAc:hexanes:AcOH=1:2:1%) gave indole-3-propionic acid as a white solid.

Yields of indole-3-propionic acid 11 were: $BOB(OAc)_4$: 71%; $BH_3$: 54%; $BOBPh_4$: 49%; $BCl_3$: 33%; $TiCl_4$: 17% and $Cl_2BOTFAc$: 16%. No reaction of indole 10 with acrylic acid was catalyzed by o-bromophenylboronic acid 5a. Acrylic acid alkylation of indole 10 catalyzed by 5 mol % $BOB(OAc)_4$ in acetonitrile afforded an 89% isolated yield of indole-3-propionic acid 11.

In addition, the reaction of indole and acrylic acid, catalyzed by $BOB(OAc)_4$, was also carried out in acetonitrile.

To a 3 mL vial containing tetraacetyl diborate (27.4 mg, 0.1 mmol) in 1 mL of ACN under air was added indole (234 mg, 2 mmol). The mixture was stirred at ambient temperature for 1 min, followed by addition of acrylic acid (165 μL, 2.4 mmol). After the reaction was completed, the crude was loaded directly onto a flash column. Chromatographic purification (EtOAc:hexanes:AcOH=1:2:1%) gave 336 mg (89%) of indole-3-propionic acid as a white solid. $^1$H NMR (500 MHz, MeOH-$d_4$) δ=2.67 (t, J=7.8 Hz, 2H), 3.05 (t, J=7.8 Hz, 2H), 6.98-7.03 (m, 2H), 7.09 (dd, J=7.6 Hz, 7.6 Hz, 1H), 7.32 (d, J=8.2 Hz, 1H), 7.53 (d, J=8.0 Hz, 1H). $^{13}$C NMR (125 MHz, MeOH-$d_4$) δ=20.4, 34.7, 110.8, 113.6, 117.8, 118.2, 120.9, 121.5, 127.1, 136.7, 176.1.

Example 5. Crystallographic Analysis of $BOB(OAc)_4$

In a 3 mL vial tetraacetyl diborate (1 mmol, 274 mg) was dissolved in 0.6 mL of DCM followed by addition of acrylic acid (1 mmol, 72 mg). The mixture was stirred at rt for 1 min followed by filtration with a syringe filter to provide a clear, colorless solution. Toluene (0.2 mL) was added slowly to the top of the DCM followed by addition of hexanes (3 mL). White solid precipitated overnight at rt. A suitable colorless plate-shaped crystal (0.35×0.20×0.03 mm) was selected and mounted on a nylon loop with paratone oil on a Bruker APEX-II CCD diffractometer. The crystal was kept at T=173 (2) K during data collection. Using Olex2, the structure was solved with the ShelXS structure solution program, using the Direct Methods solution method. The model was refined with version 2014/6 of XL using Least Squares minimization. Crystal Data: $C_8H_{12}B_2O_9$, $M_r$=273.80, monoclinic, $P2_1/c$ (No. 14), a=7.5965(15) Å, b=8.0533(18) Å, c=20.807 (4) Å, β=96.907(12)°, α=γ=90°, V=1263.7(5) Å$^3$, T=173(2) K, Z=4, Z'=1, μ(CuK$_\alpha$)=1.122, 7404 reflections measured, 2331 unique ($R_{int}$=0.0811) which were used in all calculations. The final $wR_2$ was 0.3581 (all data) and $R_1$ was 0.0975 (I>2(I)). The crystal structure is shown in FIG. 5.

In the preceding procedures, various steps have been described. It will, however, be evident that various modifications and changes may be made thereto, and additional procedures may be implemented, without departing from the broader scope of the exemplary procedures as set forth in the claims that follow.

We claim:

1. A method for producing a cycloaddition product comprising: reacting a diene with a dienophile in the presence of one or more catalysts of Formula I or Formula II;
   wherein a catalyst of Formula I has the following structure:

Formula I wherein each X, Y and Z is independently H, F, Cl, Br, I, OC(=O)R$^1$, OR$^1$, substituted or unsubstituted $C_{1-6}$ alkyl, substituted or unsubstituted $C_{6-12}$ aryl;
   wherein R$^1$ is a substituted or unsubstituted $C_{1-6}$ alkyl; or a substituted or unsubstituted $C_{6-12}$ aryl;
   wherein at least one of X, Y and Z is Cl; and
   wherein the catalyst is not $BCl_3$; and
   wherein a catalyst of Formula II has the following structure:

BOBL$_4$    Formula II wherein each L is independently selected from the group consisting of OC(=O)R$^2$, substituted or unsubstituted $C_{6-12}$ aryl, substituted or unsubstituted $C_{1-6}$ alkyl, substituted or unsubstituted $C_{5-12}$ cycloalkyl; substituted or unsubstituted $C_{1-6}$ alkylsulfonate; substituted or unsubstituted $C_{6-12}$ arylsulfonate, and substituted or unsubstituted $C_{5-12}$ heteroaryl; and
   wherein R$^2$ is a substituted or unsubstituted $C_{1-6}$ alkyl; or a substituted or unsubstituted $C_{6-12}$ aryl;
   wherein the dienophile comprises a —CH=CHC(O)OH group.

2. The method of claim 1, wherein the catalyst of Formula I is selected from the group consisting of $Cl_2B(OC(=O)CH_3)$ and $Cl_2B(OC(=O)CF_3)$.

3. The method of claim 1, wherein the catalyst of Formula II is selected from the group consisting of $BOB(OC(=O)CH_3)_4$ and $BOB(C_6H_5)_4$.

4. The method of claim 1, wherein the one or more catalysts of Formula I or Formula II comprises: $BOB(OC(=O)CH_3)_4$.

5. The method of claim 1, wherein one or both of the diene and dienophile are bio-based.

6. The method of claim 1, wherein the dienophile is a $C_3$-$C_{12}$ alkene comprising an electron-withdrawing group in conjugation with the alkene.

7. The method of claim 1, wherein the dienophile is selected from the group consisting of: acrylic acid, a β-acylacrylic acid, and any bio-derived sources thereof.

8. The method of claim 1, wherein the diene is a $C_4$-$C_{17}$ hydrocarbon that contains at least two carbon double bonds which are separated by a single bond.

9. The method of claim 8, wherein the diene is liquid at or near about 20° C. to about 25° C.

10. The method of claim 1, wherein the cycloaddition product is 4-methyl-3-cyclohexene-1-carboxylic acid.

11. A method for producing 4-methyl-3-cyclohexene-1-carboxylic acid, comprising reacting isoprene with acrylic acid in the presence of one or more catalysts of Formula I or Formula II to produce 4-methyl-3-cyclohexene-1-carboxylic acid;

wherein a catalyst of Formula I has the following structure:

Formula I wherein each X, Y and Z is independently H, F, Cl, Br, I, OC(=O)R$^1$, OR$^1$, substituted or unsubstituted $C_{1-6}$ alkyl, substituted or unsubstituted $C_{6-12}$ aryl;
wherein R$^1$ is a substituted or unsubstituted $C_{1-6}$ alkyl; or a substituted or unsubstituted $C_{6-12}$ aryl; and
wherein at least one of X, Y and Z is Cl; and
wherein the catalyst is not BCl$_3$; and wherein a catalyst of Formula II has the following structure:

BOBL$_4$       Formula II wherein each L is independently selected from the group consisting of OC(=O)R$^2$, substituted or unsubstituted $C_{6-12}$ aryl, substituted or unsubstituted $C_{1-6}$ alkyl, substituted or unsubstituted $C_{5-12}$ cycloalkyl; substituted or unsubstituted $C_{1-6}$ alkylsulfonate; substituted or unsubstituted $C_{6-12}$ arylsulfonate, and substituted or unsubstituted $C_{5-12}$ heteroaryl; and
wherein R$^2$ is a substituted or unsubstituted $C_{1-6}$ alkyl; or a substituted or unsubstituted $C_{6-12}$ aryl.

12. The method of claim 1, wherein the reaction is conducted at about ambient temperature.

13. The method of claim 11, wherein the method also produces 3-methyl-3-cyclohexene-1-carboxylic acid.

14. The method of claim 11, wherein the one or more catalysts of Formula I or Formula II comprises: BOB(OC(=O)CH$_3$)$_4$.

15. A method for producing terephthalic acid, isophthalic acid or a mixture thereof, comprising:

(a) reacting isoprene with acrylic acid in the presence of one or more catalysts of Formula I or Formula II to form 4-methyl-3-cyclohexene-1-carboxylic acid, 3-methyl-3-cyclohexene-1-carboxylic acid, or a mixtures thereof;

(b) performing an aromatization reaction on the 4-methyl-3-cyclohexene-1-carboxylic acid, 3-methyl-3-cyclohexene-1-carboxylic acid, or a mixtures thereof to form a second product selected from the group consisting of para-toluic acid, meta-toluic acid, and mixtures thereof; and (c) performing an oxidation reaction on the second product to form terephthalic acid, isophthalic acid, or mixtures thereof;

wherein a catalyst of Formula I has the following structure:

Formula I wherein each X, Y and Z is independently H, F, Cl, Br, I, OC(=O)R$^1$, OR$^1$, substituted or unsubstituted $C_{1-6}$ alkyl, substituted or unsubstituted $C_{6-12}$ aryl;
wherein R$^1$ is a substituted or unsubstituted $C_{1-6}$ alkyl; or a substituted or unsubstituted $C_{6-12}$ aryl;
wherein at least one of X, Y and Z is Cl; and
wherein the catalyst is not BCl$_3$; and
wherein a catalyst of Formula II has the following structure:

BOBL$_4$       Formula II wherein each L is independently selected from the group consisting of OC(=O)R$^2$, substituted or unsubstituted $C_{6-12}$ aryl, substituted or unsubstituted $C_{1-6}$ alkyl, substituted or unsubstituted $C_{5-12}$ cycloalkyl; substituted or unsubstituted $C_{1-6}$ alkylsulfonate; substituted or unsubstituted $C_{6-12}$ arylsulfonate, and substituted or unsubstituted $C_{5-12}$ heteroaryl; and
wherein R$^2$ is a substituted or unsubstituted $C_{1-6}$ alkyl; or a substituted or unsubstituted $C_{6-12}$ aryl.

16. The method of claim 15, wherein the one or both of isoprene and acrylic acid are bio-based.

17. The method of claim 15, wherein the aromatization reaction is conducted in the presence of sulfuric acid.

18. The method of claim 15, wherein the aromatization reaction is performed in acetic anhydride solvent.

19. The method of claim 15, wherein the aromatization reaction is conducted in the presence of a catalyst, optionally selected from the group consisting of chromium, molybdenum, iridium, rhodium, ruthenium, nickel, palladium, platinum, vanadium, iron and manganese.

20. The method of claim 15, wherein the one or more catalysts of Formula I or Formula II comprises: BOB(OC(=O)CH$_3$)$_4$.

* * * * *